(12) United States Patent
Koller et al.

(10) Patent No.: US 8,980,243 B2
(45) Date of Patent: Mar. 17, 2015

(54) SURFACE ACTIVE AGENT COMPOSITIONS AND METHODS FOR ENHANCING OXYGENATION, REDUCING BACTERIA AND IMPROVING WOUND HEALING AT A SITE OF TREATMENT

(76) Inventors: Neal Koller, Annapolis, MD (US); George Rodeheaver, Charlottesville, VA (US); Roberto Cassino, Abbiategrasso (IT)

(*) Notice: Subject to any disclaimer, the term of this patent is extended or adjusted under 35 U.S.C. 154(b) by 237 days.

(21) Appl. No.: 13/321,106

(22) PCT Filed: May 19, 2010

(86) PCT No.: PCT/US2010/035440
§ 371 (c)(1),
(2), (4) Date: May 2, 2012

(87) PCT Pub. No.: WO2010/135449
PCT Pub. Date: Nov. 25, 2010

(65) Prior Publication Data
US 2012/0207700 A1    Aug. 16, 2012

Related U.S. Application Data

(60) Provisional application No. 61/179,577, filed on May 19, 2009.

(51) Int. Cl.
| | | |
|---|---|---|
| *A61K 31/77* | (2006.01) | |
| *A61P 31/00* | (2006.01) | |
| *A61P 29/00* | (2006.01) | |
| *A61P 17/02* | (2006.01) | |
| *A61K 31/74* | (2006.01) | |
| *A61K 9/00* | (2006.01) | |
| *A61K 9/06* | (2006.01) | |
| *A61K 9/08* | (2006.01) | |
| *A61K 9/70* | (2006.01) | |
| *A61K 31/14* | (2006.01) | |
| *A61K 31/785* | (2006.01) | |
| *A61K 33/18* | (2006.01) | |
| *A61K 33/38* | (2006.01) | |
| *A61K 45/06* | (2006.01) | |
| *A61K 47/34* | (2006.01) | |

(52) U.S. Cl.
CPC ............. *A61K 31/74* (2013.01); *A61K 9/0014* (2013.01); *A61K 9/06* (2013.01); *A61K 9/08* (2013.01); *A61K 9/7007* (2013.01); *A61K 31/14* (2013.01); *A61K 31/77* (2013.01); *A61K 31/785* (2013.01); *A61K 33/18* (2013.01); *A61K 33/38* (2013.01); *A61K 45/06* (2013.01); *A61K 47/34* (2013.01)
USPC ...................................................... 424/78.3

(58) Field of Classification Search
None
See application file for complete search history.

(56) References Cited

U.S. PATENT DOCUMENTS

| | | |
|---|---|---|
| 4,920,158 A | 4/1990 | Murray et al. |
| 5,284,833 A | 2/1994 | McAnalley et al. |
| 5,298,260 A | 3/1994 | Viegas et al. |
| 5,326,567 A | 7/1994 | Capelli |
| 5,607,683 A | 3/1997 | Capelli |
| 5,804,213 A | 9/1998 | Rolf |
| 6,039,965 A | 3/2000 | Donlan et al. |
| 6,096,225 A | 8/2000 | Yang et al. |
| 6,096,324 A * | 8/2000 | Mansouri ................ 424/401 |
| 6,110,381 A | 8/2000 | Wright |
| 6,149,822 A | 11/2000 | Fabri et al. |
| 6,201,065 B1 | 3/2001 | Pathak et al. |
| 6,328,991 B1 * | 12/2001 | Myhling ................ 424/430 |
| 6,395,189 B1 | 5/2002 | Fabri et al. |
| 6,399,092 B1 * | 6/2002 | Hobson et al. ............. 424/443 |
| 6,410,645 B1 | 6/2002 | Pathak et al. |
| 6,440,437 B1 | 8/2002 | Krzysik et al. |
| 6,585,961 B1 | 7/2003 | Stockel |
| 6,723,688 B1 * | 4/2004 | Malik et al. ............... 510/130 |
| 6,903,243 B1 | 6/2005 | Burton |
| 6,927,237 B2 | 8/2005 | Hei et al. |
| 6,977,082 B2 | 12/2005 | Seitz, Jr. et al. |
| 7,083,806 B2 | 8/2006 | Rippon et al. |
| 7,144,992 B2 | 12/2006 | Madhyastha |
| 7,976,875 B2 | 7/2011 | Myntti |
| 2005/0079147 A1 * | 4/2005 | Delaey et al. ............ 424/78.08 |
| 2005/0271604 A1 | 12/2005 | Gestrelius et al. |
| 2006/0018945 A1 | 1/2006 | Britigan et al. |
| 2006/0052452 A1 | 3/2006 | Scholz |
| 2006/0246075 A1 | 11/2006 | Mercken et al. |
| 2007/0093517 A1 * | 4/2007 | Newton ................... 514/282 |

(Continued)

FOREIGN PATENT DOCUMENTS

| | | |
|---|---|---|
| CA | 2599653 | 9/2006 |
| DE | 10238450 | * 8/2004 ............... A61K 7/00 |

(Continued)

OTHER PUBLICATIONS

Baskaran, H. et al. "Poloxamer-188 Improves Capillary Blood Flow and Tissue Viability in a cutaneous burn wound." Journal of Surgical Research, 2001, v. 101, 56-61.*

Birchenough, S. A.; et al. "Topical poloxamer-188 improves blood flow following thermal injury in rat mesenteric microvasculature." Annals of Plastic Surgery, 2008, 60, 584-588.*

Supplementary European Search Report dated Jan. 23, 2013 for corresponding application EP 10778342.

International Search Report and Written Opinion of the International Searching Authority, Jul. 13, 2010, from parent foreign application PCT/US2010/035440, International Filing Date May 19, 2010.

(Continued)

*Primary Examiner* — Sue Liu
*Assistant Examiner* — Erin Hirt
(74) *Attorney, Agent, or Firm* — Pepper Hamilton LLP

(57) ABSTRACT

This present invention relates generally to the use of novel formulations comprising a surface active polymer to enhance oxygenation in skin and other soft tissue. The present invention also discloses formulations that can be used to improve clinical outlook and reducing bacteria. Methods of making and using the same are also disclosed.

1 Claim, No Drawings

(56) References Cited

U.S. PATENT DOCUMENTS

| | | |
|---|---|---|
| 2007/0258996 A1 | 11/2007 | Mookerjee et al. |
| 2008/0031831 A1 | 2/2008 | Laali |
| 2009/0202615 A1 | 8/2009 | Rodeheaver et al. |
| 2009/0226541 A1 | 9/2009 | Scholz et al. |
| 2013/0101661 A1 | 4/2013 | Rodeheaver et al. |

FOREIGN PATENT DOCUMENTS

| | | |
|---|---|---|
| WO | WO 01/21195 A1 | 3/2001 |
| WO | WO 01/85845 A1 | 11/2001 |
| WO | WO 2004/037115 A2 | 5/2004 |
| WO | WO 2006/099359 A2 | 9/2006 |
| WO | WO 2007/087806 A1 | 8/2007 |
| WO | 2008034138 A1 | 3/2008 |
| WO | WO 2008/103673 A1 | 8/2008 |
| WO | 2008154368 A2 | 12/2008 |
| WO | WO 2010/135449 A1 | 11/2010 |

OTHER PUBLICATIONS

International Preliminary Report on Patentability and Written Opinion of the International Searching Authority, Dec. 1, 2011, from counterpart foreign application PCT/US2010/035440.

Ali et al., Investigating the suitability of the Calgary Biofilm device for assessing the antimicrobial efficacy of new agents, 2006, *Biosource Technology* 97:1887-1893.

B Braun Medical AG, "B Braun—Infection Control, Wound Care, Instrument Preparation and Surface Disinfection," Apr. 12, 2006, SPG Media Limited, London, United Kingdom, http://www.hospitalmanagement.net/contractors/cleaning/b-braun/.

Ceri et al., The Calgary Device: New Technology for the Rapid Determination of Antibiotic Susceptibilities of Bacterial Biofilms, 1999, *J. Clin. Microbio.* 7(6):1771-1776.

Ceri et al., The MBEC Assay System: multiple equivalent biofilms for antibiotic and biocide susceptibility testing methods, 2001, *Enzymol.* 337:377-385.

Chandra et al., Antifungal Resistance of Candidal Biofilms Formed on Denture Acrylic in vitro, 2001, *J. Dental Research* 80(3):903-908.

Chiu et al., Evaluation of the in vivo efficacy of topical tobramycin against Pseudomonas sinonasal biofilms, 2007, *J. Antimicrobial Chemotherapy* 59(6):1130-1134.

Costerton et al., Microbial biofilms, 1995, *Ann, Rev. Microbiol.* 49:711-745.

Effective Wound Cleansing, Mar. 2007, *The Clinical Services Journal*, Kent, United Kingdom, http://www.clinicalservicesjournal.com/Print.aspx?Story=2104.

Extended European Search Report dated Oct. 22, 2012 for EP 08730165.1.

Frank et al., In Vitro Effects of Antimicrobial Agents on Planktonic and Biofilm Forms of *Staphylococcus lugdunensis* Clinical Isolates, 2007, *Antimicrobial Agents and Chemotherapy* 51(3):888-895.

Goto et al., In Vitro Bactericidal Activities of Beta-Lactamases, Amikacin, and Fluoroquinolones Against *Pseudomonas aeruginose* Biofilm in Artificial Urine, 1999, *Urology* 53(5):1058-1062.

Horrocks, Ann, "Prontosan Wound Irrigation and Gel: Management of Chronic Wounds," *British Journal of Nursing*, vol. 15, Iss. 22, Dec. 14, 2006, pp. 1222-1228, London, United Kingdom, http://www.internurse.com/cgi-bin/go.pl/library/article.cgi?uid-22559; article=BJN_15_22_1222_1228.

Marsh, Plaque as a biofilm: pharmacological principles of drug delivery and action in the sub- and supragingival environment, 2003, *Oral Diseases* 9(1):16-22.

Melchior et al., Comparative Assessment of the Antimicrobial Susceptibility of *Staphylococcus aureus* Isolates from Bovine Mastitis in Biofilm Versus Planktonic Culture, 2006, *J. Veterinary Medicine Series B* 53(7):326-332.

Nickel et al., Tobramycin resistance of *Pseudomonas* aeruginose cells growing as a biofilm on urinary catheter material, 1985, *Antimicrob, Agents Chemother.* 27(4):619-624.

Nickel, et al., Bacterial biofilms and catheters: a key to understanding bacterial strategies in catheter-associated urinary tract infection, Sep./Oct. 1992, Can J. Infect Dis vol. 3 No. 5, 261-267.

Olson et al., Biofilm Bacteria: formation and comparative susceptibility to antibiotics, 2002, *Canadian J. Veterinary Research* 66:86-92.

Paulson, Efficacy of preoperative antimicrobial skin preparation solutions on biofilm bacteria, 2005, *AORN Journal* 81(3):503-506.

Rodeheaver et al., Pharmacokinetics of a New Skin Wound Cleanser, *American Journal of Surgery*, (Jul. 1, 1976), 132(1):67-74.

Sedlacek et al., Antibiotic resistance in an in vitro subgingival biofilm model, 2007, *Oral Microbiology & Immunology* 22(5):333-339.

Surdeau et al., Sensitivity of bacterial biofilms and planktonic cells to a new antimicrobial agent, Oxsil 320N, 2006, *J. Hospital Infection* 62(4):487-493.

Wesenberg-Ward et al., Adhesion and Biofilm Formation of *Candida Albicans* on Native and Pluronic-treated Polystyrene, *Biofilms*, (Jan. 1, 2005), 2(1):63-71 (Abstract).

Yousef et al., Inhibition of Bacterial Adherence and Biofilm on Contact Lenses, *Egypt. J. Biomed. Sci.* (1998), 1, 79-94 (Abstract).

* cited by examiner

SURFACE ACTIVE AGENT COMPOSITIONS AND METHODS FOR ENHANCING OXYGENATION, REDUCING BACTERIA AND IMPROVING WOUND HEALING AT A SITE OF TREATMENT

CROSS-REFERENCE TO RELATED APPLICATIONS

This application is a U.S. National Stage filing under 35 U.S.C. §371 of International Application No. PCT/US2010/035440, filed May 19, 2010, which claims the benefit of and priority to U.S. Provisional Application No. 61/179,577, filed on May 19, 2009, each of which is hereby incorporated by reference in its entirety.

GOVERNMENT INTERESTS

Not Applicable

PARTIES TO A JOINT RESEARCH AGREEMENT

Not Applicable

INCORPORATION BY REFERENCE 0° F. MATERIAL SUBMITTED ON A COMPACT DISC

Not Applicable

BACKGROUND

Poloxamers are water-soluble triblock copolymers composed of hydrophilic polyethylene oxide (PEO) and hydrophobic polypropylene oxide (PPO) blocks linked together. The amphiphilic nature of these block copolymers can be varied by controlling the length of the PEO and/or PPO block components (Ahmed et al., 2001). Several members of this poloxamer family of chemicals (such as poloxamer 188 and 407 are known to be biocompatible and non-toxic to mammalian cells and tissues, making them useful fir biomedical applications. These compounds are surface acting (or "surface active") agents (i.e. "surfactants") and known to incorporate into or onto mammalian cell membranes, and thereby reduce protein adsorption and cell adhesion.

The skin serves as a protective barrier against the environment. The skin serves as a barrier to infection and prevents the loss of water and electrolytes from the body. Thus, the loss of the integrity of large portions of the skin as a result of illness or injury can lead to major disability or even death.

Every year in the United States there are 1.1 million burn patients who require medical attention and 6.5 million patients are reported to have chronic skin ulcers caused by pressure, venous stasis, or diabetes mellitus. Thus, acceleration of skin wound healing has been an active area of medical research and improved designs of skin repair materials have been sought for decades.

There is a long felt need in the art for compositions and methods useful for treating injuries and wounds topically. The present invention addresses the need by providing novel formulations and methods of treating skin and other soft tissues that enhance oxygenation, reduce bacteria at the treated site, improve healing, and any combination thereof.

SUMMARY 0° F. THE INVENTION

In some embodiments, the present invention provides methods of increasing oxygenation at a site on a subject comprising contacting a site with a first composition comprising at least one surface active agent and optionally at least one additional therapeutic agent, wherein upon contacting the site with the composition the site has increased oxygenation. In some embodiments the site has been identified as a site needing increased oxygenation. In some embodiments, the subject is a subject in need of increased oxygenation at said site. In some embodiments, the at least one surface active agent is a surface active copolymer. Iii some embodiments, the composition comprises, about 0-10% w/w of the surface active agent. In some embodiments, the composition comprises about 5% w/w of said surface active agent.

In some embodiments, the present invention provides compositions for treating a site to increase oxygenation, reduce bacterial count, and/or increase healing at the treated site on a subject comprising at least one surface active agent and optionally at least one additional therapeutic agent. In some embodiments, the compositions are liquids or gels.

In some embodiments, the present invention provides fabric materials comprising a composition comprising at least one surface active agent and optionally at least one additional therapeutic agent. In some embodiments, the at least one surface active agent is an surface active copolymer. In sonic embodiments, the fabric materials are used to increase oxygenations, reduce bacterial count, or improve wound healing at a site on a subject.

DESCRIPTION 0° F. DRAWINGS

None

DETAILED DESCRIPTION

This invention relates generally to the use of novel formulations comprising a surface active polymer to enhance oxygenation in skin and other soft tissue. The formulations can also be used to improve clinical outlook, including to improve heating and reduce bacteria.

As used herein, the term "composition" can also be referred to as a formulation. The composition can consist of one ingredient or comprise more than one ingredients. The number of components or ingredients does not differentiate between a composition or a formulation, in some embodiments, the composition is a pharmaceutical composition. In some embodiments, the composition is a therapeutic composition.

The present invention is based on the discovery described herein that the administration (e.g. topical) of a composition comprising a surface active copolymer such as a poloxamer can be used, in some embodiments, to increase oxygenation, reducing bacteria, and/or improving healing at a tissue site, and any combination thereof. In some embodiments, the present invention provides compositions and methods for increasing oxygenation, reducing bacteria, and/or improving healing at a treated site. In some embodiments, the compositions can be used to increase oxygenation, reduce bacteria, and/or improve healing at the site of specific injuries or at sites associated with certain diseases and conditions. The compositions and methods can also benefit healthy skin and other soft tissue. Without wishing to be bound by theory, it is hypothesized that the surfactant component acts as an oxygen reservoir and/or delivery vehicle to increase oxygenation, reduce bacteria, and improve healing at a treated site.

In some embodiments, the present invention provides methods of treating a tissue site. In some embodiments, the method comprises applying (e.g. topically) to the tissue site a pharmaceutical composition comprising a surfactant and optionally at least one additional therapeutic agent. In some embodiments, the amount of the composition that is applied is an amount effective to increase oxygenation, reduce bacteria and/or improve healing at the tissue site. In some embodiments, the composition comprises at least one surface active copolymer and optionally at least one additional therapeutic agent to increase oxygenation, reduce bacteria and/or improve healing at the tissue site.

In some embodiments, the at least one surface active copolymer is a poloxamer, a meroxapol, or a poloxamine. In some embodiments, the pharmaceutical composition comprises poloxamer 188.

Disclosed herein are formulations of surfactants, for example, poloxamers or other surface active agents for delivery (e.g., topical) to healthy, injured and/or diseased tissues. The formulations can be used to enhance oxygenation, reduce bacteria and/or improve healing, in some embodiments, wounds (e.g. chronic or acute) treated with the formulations disclosed herein demonstrate increased oxygenation, or improved clinical outlook, which can include improved healing and/or reduction in bacteria at the site of the wound.

In some embodiments, the present invention provides compositions comprising at least one surface active copolymer and methods of treating a site of injury (e.g., burn injury, chronic wounds, skin grafts or other injury to skin or soft tissue) or exposed soft tissue using the compositions or formulations disclosed herein. In some embodiments, the surface active copolymers include, but are not limited to, poloxamers, meroxapols, and poloxamines.

In some embodiments, a composition or formulation disclosed herein comprises at least one surface active copolymer or surface active agent at about 0.01%-85% In some embodiments, a composition or formulation disclosed herein comprises at least one surface active copolymer or surface active agent at about 0.01%-75% w/w. In some embodiments, composition or formulation disclosed herein comprises at least one surface active copolymer or surface active agent at about 0.01%-0.1%, about 0.01%-0.5%, or about 0.01%4.0% w/w. In some embodiments, a composition or formulation disclosed herein comprises at least one surface active copolymer or surface active agent at about 0.01%, about 0.02%, about 0.03%, about 0.04%, about 0.05%, about 0.06%, about 0.07%, about 0.08%, or about 0.09% w/w. In some embodiments, a composition or formulation disclosed herein comprises at least one surface active copolymer or surface active agent at about 0.01%-60% about 0.010% w/w, about 0.01%-50% w/w, about 0.01%40% w/w, about 0.01%-30% w/w, about 0.01%-20% w/w, about 0.01%-10% w/w, about 0.01%-5% w/w, about 0.01%-3%, 0.5%-60% w/w, about 0.5%-50% w/w, about 0.5%-50% w/w, about 0.5%-40% w/w, about 0.5%-30% w/w, about 0.5%-20% w/w, about 0.5%-10% about 0.5%-5% w/w, about 0.5%-3% w/w, about 5%-10% w/w, about 4%-6% about 4%-5% w/w, about 5%-15% w/w, about 0.1%, about 0.2%, about 0.3%, about 0.4%, about 0.5%, about 0.6%, about 0.7%, about 0.8%, about 0.9%, about 1% w/w, about 2% w/w, about 3% w/w, about 4% w/w, about 5% w/w, about 6% w/w, about 7% w/w, about 8% w/w, about 9% w/w, or about 10% w/w.

Additional components optionally may be present in the compositions or formulations in the ranges shown in the table below, with the balance being supplied by water or another solvent. Appropriate ingredient substitutions may be made based on the type of ingredient, as would be understood by one of skill in the art.

| | | |
|---|---|---|
| *Aloe Barbadensis* Leaf Extract | 0-30% | Anti-inflammatory |
| Linoleamidopropyl Pg-Dimonium Chloride Phosphate | 0-20% | Surfactant & moisturizer |
| Polysorbate 20 | 0-10% | Surfactant |
| Sodium Coco-Pg Dimonium Chloride Phosphate | 0-30% | Surfactant & moisturizer |
| Allantoin | 0-20% | Moisturizer |
| Disodium EDTA | 0-5% | Surfactant |
| Sodium Benzoate | 0-5% | Preservative |
| Benzalkonium Chloride | 0-5% | Preservative |
| Fragrance | 0-5% | Fragrance |
| Iodopropynyl Butylcarbamate | 0-5% | Preservative |
| Poloxamer 188 | 0.01-85% | Surfactant |

In some embodiments, the composition comprises about 0-30%, about 0-20, about 0-15, about 0-10, about 0-5, about 5-10, about 15-2.0, about 10-15, about 1-3, about 3-5, about 5-7, about 7-9, about 9-11, about 1, about 2, about 3, about 4, about 5, about 6, about 7, about 8, about 9, about 10, about 11, about 12, about 13, about 14, about 15, about 16, about 17, about 18, about 19, about 20, about 2.1, about 22, about 23, about 24, about 25, about 26, about 27, about 28, about 29, about 30% w/w *Aloe barbodensis* leaf extract.

In some embodiments, the composition comprises about 0-20, about 0-15, about 0-10, about 0-5, about 5-10, about 15-20, about 10-15, about 1-3, about 3-5, about 5-7, about 7-9, about 9-11, about 1, about 2, about 3, about 4, about 5, about 6, about 7, about 8, about 9, about 10, about 11, about 12, about 13, about 14, about 15, about 16, about 17, about 18, about 19, or about 20 w/w linoleamidopropyl pg-dimonium chloride phosphate.

In some embodiments, the composition comprises about 0-10, about 0-5, about 0-4, about 0-3, about 0-2, about 0-1, less than 1, about 5-10, about 1-3, about 3-5, about 5-7, about 7-9, about 9-10, about 1, about 2, about 3, about 4, about 5, about 6, about 7, about 8, about 9, or about 10% w/w polysorbate 20.

It some embodiments, the composition comprises about 0-30%, about 0-20, about 0-15, about 0-10, about 0-5, about 0-4, about 0-3, about 0-2, about 0-1, less than 1, about 5-10, about 15-20, about 10-15, about 1-3, about 3-5, about 5-7, about 7-9, about 9-11, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 w/w sodium coco-pg dimonium chloride phosphate.

In some embodiments, the composition comprises about 0-20, about 0-15, about 0-1.0, about 0-5, about 0-4, about 0-3, about 0-2, about 0-1, about 5-10, about 15-20, about 10-15, about 1-3, about 3-5, about 5-7, about 7-9, about 9-11, about 1, about 2, about 3, about 4, about 5, about 6, about 7, about 8, about 9, about 10, about 11, about 12, about 13, about 14, about 15, about 16, about 17, about 18, about 19, or about 20% w/w allantoin.

In some embodiments, the composition comprises about 0-5, about 0-4, about 0-3, about 0-2, about 0-1 less than 1, about 1-3, about 3-5, about 1, about 2, about 3, about 4, or about 5% w/w disodium EDTA.

In some embodiments, the composition comprises about 0-5, about 0-4, about 0-3, about 0-2, about 0-1, less than 1 about 1-3, about 3-5, about 1, about 2, about 3, about 4, or about 5% w/w sodium benzoate.

In some embodiments, the composition comprises about 0-5, about 0-4, about 0-3, about 0-2, about 0-1, less than 1, about 1-3, about 3-5, about 1, about 2, about 3, about 4, or about 5% w/w benzalkonium chloride.

In some embodiments, the composition comprises about 0-5, about 0-4, about 0-3, about 0-2, about 0-1, less than 1, about 1-3, about 3-5, about 1, about 2, about 3, about 4, or about 5% w/w fragrance.

In some embodiments, the composition comprises about 0-5, about 0-4, about 0-3, about 0-2, about 0-1, less than 1, about 1-3, about 3-5, about 1, about 2, about 3, about 4, or about 5% w/w iodopropynyl butylcarbamate.

The therapeutic compositions of the invention may be formulated, for example, as liquids or as stable gels.

In some embodiments, the compositions or formulations disclosed herein are used to treat various injuries, diseases, and disorders which are characterized by reduced oxygen levels or that would benefit from increased oxygen levels. Examples of various injuries, diseases, and disorders which are characterized by reduced oxygen levels or that would benefit from increased oxygen levels include, but are not limited to, thermal injury, skin injury, soft tissue injury, non-healing skin wound, burns, acute wound, chronic wound, scrape, cut, incision, laceration, decubitis, pressure deer, chronic venous ulcer, venous stasis ulcer, diabetic ulcer, arterial ulcer, radiation ulcer, traumatic wound, open complicated non-healing wound, body piercing, bite wound, insect bite, insect sting, stab wound, gunshot wound, stretch injury, crush wound, compression wound, fracture, sprain, strain, stroke, infarction, aneurism, herniation, ischemia, fistula, dislocation, radiation, surgery, cell, tissue or organ grafting, and cancer.

In some embodiments, the present invention provides compositions and methods for increasing oxygenation, reducing bacteria and/or improving healing of tissue a site treated by administering an effective amount of a composition or formulation describes herein to a site (e.g., a site of injury). Examples of injuries, including burns include, but are not limited to thermal burns, radiation burns, chemical burns, electrical burns, steam horns, and sunburn. In some embodiments, the burn is a thermal injury. In some embodiments, the thermal injury is a cutaneous injury or an injury of the mesentery of the intestine.

In some embodiments, the composition or formulation comprises at least 1, at least 2, at least 3, at least 4, or at least 5 surface active copolymers. In some embodiments, the composition or formulation comprises 1, 2, 3, 4, or 5 surface active copolymers.

In some embodiments, the invention provides compositions or formulations and methods for increasing oxygenation, reducing bacteria, and/or improving healing in chronic wounds by administering an effective amount of the compositions or formulations disclosed herein to a site of a chronic wound. Chronic wounds include, for example, but are not limited to, venous stasis ulcers, diabetic wounds, arterial ulcers, and pressure ulcers.

In some embodiments, the present invention provides compositions or formulations and methods for increasing oxygenation, reducing bacteria, and/or improving healing in skin or tissue following a surgical procedure, for example, skin grafts, microvascular surgery and tissue flaps, by administering an effective amount of the compositions or formulations disclosed herein to the site.

The route of administration or method of application can vary depending on the formulation or composition being administered as well as on the site of injury, disease, or disorder being treated. In some embodiments, an method of topical administration of the composition or formulations disclosed herein can be used to treat the injuries, diseases, and disorders disclosed herein. In some embodiments, the compositions or formulations can be administered via routes, including, but not limited to, direct, topical, cutaneous, mucosal, nasal, inhalation, oral, and ophthalmic. Methods of applying or administration include, but are not limited to contacting the site with a dressing material, extruder, aerosol, spray delivery, iontophoresis, a patch, a wipe, or a transdermal patch. The dressing material, extruder, aerosol, spray delivery, iontophoresis, a patch, a wipe, or a transdermal patch can comprise any composition or formulation described herein.

In some embodiments, the compositions, formulations, additional therapeutic agent, or another compound are administered as a controlled-release formulation.

The dosage of the active compound(s) being administered will depend on the condition being treated, the particular compound, and other clinical factors such as age, sex, weight, and health of the subject being treated, the route of administration of the compound(s), and the type of composition being administered (gel, liquid, solution, suspension, aerosol, ointment, lotion, cream, paste, liniment, etc.). It is to be understood that the present invention has application for both human and veterinary use.

In some embodiments, the compositions or formulations described can be administered at different times before and after an injury or surgical procedure, as well as varying the optional additional therapeutic agents and the surface active copolymers.

In some embodiments, the composition or formulation described herein comprises at least one poloxamer or other surface active copolymer agent at a concentration ranging from about 0.01% to about 85% w/w or at other % w/w as disclosed herein. Examples of poloxamers include, but are not limited to, poloxamer-101, -105, -105 benzoate, -108, -122, -1.23, -124, -181, -182, -182 dibenzoate, -183, -184, -185, -188, -212, -215, -217, -231, -234, -235, -237, -238, -282, -288, -331, -333, -334, -335, -338, -401, -402, -403, and -407. In some embodiments, the poloxamer is poloxamer-188. In some embodiments, the poloxamer is poloxamer-407.

In some embodiments, composition or formulation comprises poloxamer 188 and benzalkonium chloride.

In some embodiments, the surface active copolymers is a meroxapol. Exemplary meroxapols include, but are not limited to meroxapol 105, 108, 171, 172, 174, 178, 251, 252, 254, 258, 311, 312, and 314.

In some embodiments, the surface active copolymer is a poloxamine. Exemplary poloxamines include, but are not limited to, poloxamine 304, 504, 701, 702, 704, 707, 901, 904, 908, 1101, 1102, 1104, 1301, 1302, 1304, 1307, 1501, 1502, 1504, and 1508.

In some embodiments, the composition (e.g. therapeutic or pharmaceutical) is formulated as a liquid or stable gel. The copolymer size may range, for example, from an $M_n$ of about 600 to about 20,000. In some embodiments, the copolymer size may range, for example, from an $M_n$ of about 1,000 to about 10,000.

In some embodiments, the present invention encompasses a composition comprising a surface active copolymer (e.g., a poloxamer, poloxamine, or meroxapol) at about 0.01% to about 85% w/w, or about 1% to about 65%, or about 1% to about 50%, or about 5% to about 40%, or about 10% to about 40%. The surface active copolymer can also be used at other % w/w as disclosed herein.

The surface active copolymers may be prepared at different temperatures depending on the type of formulation or composition being prepared, the route of administration, the site of administration, etc. In some embodiments, the surface active copolymer is prepared at a temperature ranging from about 0° F. to about 70° F. In some embodiments, the surface active copolymer is prepared at a temperature ranging from about 5° F. to about 50° F. In some embodiments, the surface active copolymer is prepared at a temperature ranging from about 10° F. to about 40° F. in some embodiments, the surface active copolymer is prepared at a temperature ranging from about −10° F., to about 70° F., −10° F. to about 60° F., −10° F. to about 50° F., −10° F. to about 40° F., −10° F. to about 30° F., −10° F. to about 20° F., −10° F. to about 10° F., −10° F., to about 0° F. In some embodiments, the surface active copolymer is prepared at a temperature that is less than or equal to 0° F. In some embodiments, the surface active copolymer is prepared at a temperature that is less than or equal to −1° F. In some embodiments, the surface active copolymer is prepared at a temperature that is less than or equal to −5° F.

The composition may further comprise an effective amount of at least one additional therapeutic agent. In some embodiments, the at least one additional therapeutic agent can be useful for the type of injury, disease, or disorder being treated. Additional therapeutic agents include, but are not hunted to, anesthetic, analgesic, antimicrobial, steroid, growth factor, cytokine, and anti-inflammatory agents. Anesthetic agents include, but are not limited to, benzocaine, lidocaine, bupivocaine, dibucaine, mepivocaine, etidocaine, tetracaine, butanilicaine, and trimecaine. In some embodiments, at least one additional therapeutic agent is at least one analgesic. In some embodiments, the at least one additional therapeutic is present in an amount that is less than about 1% by weight of the composition. In sonic embodiments, the at least one additional therapeutic is present in an amount that is less than about 0.95% by weight of the composition. In some embodiments, the at least one additional therapeutic is present in an amount that is less than about 0.75% by weight of the composition.

In some embodiments, the additional therapeutic agent is an antimicrobial agent. In some embodiments, the antimicrobial agent is an antibacterial agent. In some embodiments, the antimicrobial agent is an antifungal agent. In some embodiments, the antimicrobial agent is an antiviral agent. Antimicrobial agents include, but are not limited to, silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine. In some embodiments, the antimicrobial is an antimicrobial other than Nystatin. In some embodiment, the additional therapeutic agent is aspirin, pentoxifylline, clopidogrel bisulfate, or other angiogenic, or a rheologic active agent, in some embodiments, the composition comprises a "sub-lethal" amount of an antimicrobial.

As used herein the terms "sub-lethal dose" or "sub-lethal amount" refers to an amount of an antimicrobial agent or additional therapeutic that is less than the standard therapeutically effective amount. In the context of the invention described herein, a sub-lethal amount of an antimicrobial agent may effectively eradicate or inhibit the growth of a microorganisms or pathogens at the site being treated. For example, a sub-lethal amount of an antimicrobial agent in some embodiments may be from about 10% to greater than about 50% less than the standard therapeutically effective amount or 10%, 15%, 20%, 25%, 30%, 35%, 40%, 45% or 50% less than the standard therapeutically effective amount approved by a regulatory agency. In some embodiments, a sub-lethal amount may be greater than 50% less than the standard therapeutically effective amount.

For example, a standard therapeutically effective amount of a silver stilfadiazine is about 1.0% by weight when used in an antimicrobial cream or gel. However, when silver sulfadiazine is administered in combination with a surface active agent, the amount of silver sulfadiazine in the composition may be decreased below the standard therapeutically effective amount to, for example, less than 1.0% by weight. Therefore, a sub-lethal amount of silver sulthdiazine in some embodiments, may be less than 0.95 by weight, less than 0.90% by weight, less than 0.85% by weight, less than 0.80% by weight, less than 0.75% by weight, less than 0.70% by weight, less than 0.65% by weight, less than 0.60% by weight or less than 0.55% by weight of the composition, In some embodiments, the amount of silver sulfadiazine may be less than 0.5% by weight of the composition.

In some embodiments, the present invention provides methods of treating a site of injury on a subject comprising administering a composition or formulation as described herein to the subject in an amount effective to increase oxygen at the treated site. In some embodiments, the subject or the site is identified as needing to have increased oxygen at the treated site prior to the administration of a composition or formulation described herein. In some embodiments, the composition or formulation comprises a poloxamer.

Depending on such things as the type of formulation or composition being prepared, the location to which it is to be applied, and the type of injury, disease, or disorder being treated, other agents can be added to the formulation or composition. For example, other additives may include, a moisturizer, a humectant, a demulcent, oil, water, an emulsifier, a thickener, a thinner, an additional surface active agent, a fragrance, a preservative, an antioxidant, a hydrotropic agent, a chelating agent, a vitamin, a mineral, a permeation enhancer, a cosmetic adjuvant, a bleaching agent, a depigmentation agent, a foaming agent, a conditioner, a viscosifier, a buffering agent, and/or a sunscreen.

In some embodiments, the present invention provides administering cells, e.g., to a site of injury, disease, or disorder being treated. In some embodiments, the cells are part of the composition being administered, in some embodiments, the cells are applied separately (e.g., prior to or after the composition has been administered). Examples of cells include, but are not limited to, stem cells, pluripotent stem cells, committed stem cells, embryonic stein cells, adult stem cells, bone marrow stem cells, adipose stem cells, umbilical cord stem cells, dura mater stem cells, precursor cells, differentiated cells, osteoblasts, myoblasts, neuroblasts, fibroblasts, glioblasts, germ cells, hepatocytes, chondrocytes, keratinocytes, melanocytes, smooth muscle cells, cardiac muscle cells, connective tissue cells, glial cells, epithelial cells, endothelial cells, hormone-secreting cells, cells of the immune system, normal cells, Schwann cells, and neurons. In some embodiments, it is unnecessary to pre-select the type of stem cell that is to be used, because, in part, many types of stem cells can be induced to differentiate in an organ specific pattern once delivered to a given organ or tissue. In sonic embodiments, the type of stem cell is pre-selected. In some embodiments, at least two different cells are used.

In some embodiments, the present invention provides methods for identifying compounds which are useful for treating decreased oxygen levels associated with an injury, disease, or condition. In some embodiments, the present invention provides methods for identifying agents that can enhance the usage of the formulations and compositions described herein. For example, one can contact a site with a composition or formulation described herein to increase oxygen levels at the site. A test agent can be contacted at the site and the level of oxygenation is determined. If the level of oxygenation is increased then the test agent is said to enhance the formulation or composition's ability to increase oxygenation. The same method can be used to determine agents that inhibit the ability to increase oxygenation. The same method can be modified to test for agents that can enhance or inhibit bacterial growth or colonization at the site. In contrast to the method for enhancing oxygenation, the method can be used to determine bacteria at the site. Methods of determining bacterial growth or oxygenation are well known to one of skill in the art and any method can be used. Reduction in bacterial can be determined by determining the number of bacteria that are present at the site before and after contact with a composition. For example, the number of bacteria can be determined by obtaining a sample from the site and culturing the site to determine the number of bacteria. The number of bacteria can be determined by, for example, colony formation assays, optical density, and the like. A reduction in number indicates that the composition has reduced the bacteria count at the site. In some embodiments, the bacterial count is reduced by at least 5, 10, 15, 20, 25, 30, 40, 45, or 50%, in some embodiments, the bacterial count is reduced by about 5 to about 25%.

As used herein "improved healing" can refer to increased healing or the healing rate that would occur without the presence of a composition disclosed herein. Healing can be measured, for example, by viewing the wound and determining the rate of wound area reduction. The improved healing can also be determined by determining the amount of wound area reduction. Wound area reduction can be determined using any system or method including, but not limited to, the Visitrak™ system (Smith & Nephew), a wound measurement device. In some embodiments, the wound area is reduced by at least 5, 10, 15, 20, 30, 40, or 50%.

The present invention further provides kits for administering, pharmaceutical compositions of the invention to subjects in need thereof. The methods described herein can be also be used for treating subjects in need of treatment of the various disorders, conditions, and diseases.

Abbreviations and Acronyms

ASC—adipose tissue-derived stem cell
    ECM—extracellular matrix
    ES—embryonic stem cell
    FACS—fluorescent activated cell sorting
    FBS—fetal bovine serum
    FGF—fibroblast growth factor
    gf—growth factor
    HSC—hematopoietic stem cell
    IL-1β—interleukin-1 beta
    PDGF—platelet-derived growth factor
    PLA—processed lipoaspirate cells
    SCGF-β—stem cell growth factor-β
    SFM—serum-free medium
    TNFα—tumor necrosis factor alpha
    VEGF—Vascular endothelial growth factor The following terminology will be used in accordance with the definitions set forth below. Unless defined otherwise, all technical and scientific terms used herein have the same meaning as commonly understood by one of ordinary skill in the art to which this invention belongs. Additionally any methods and materials similar or equivalent to those described herein can be used in the practice or testing of the methods, compositions, or formulations described herein.

Specific values listed below for radicals, substituents, and ranges are for illustration only; they do not exclude other defined values or other values within defined tames for the radicals and substituents.

As used herein, the singular forms "a," "an," and "the" include plural reference unless the context clearly dictates otherwise.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In some embodiments, the term "about" means plus or minus 20% of the numerical value of the number with which it is being used. Therefore, about 50% can mean in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." One of skill in the art would also understand that where the present specification refers to a value with the term about, this is also discloses the specific value (e.g. about 5 discloses 5).

The terms "additional therapeutically active compound" or "additional therapeutic agent," as used herein, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. The additional compounds may also be used to treat symptoms associated with the injury, disease or disorder, including, but not limited to, pain and inflammation.

Adipose-derived stein cells (ASC) or "adipose-derived stromal cells" refer to cells that originate from adipose tissue. "Adipose" refers to any fat tissue. The adipose tissue may be brown or white adipose tissue, derived from subcutaneous, omental/visceral, mammary, gonadal, or other adipose tissue site. In some embodiments, the adipose is subcutaneous white adipose tissue. Such cells may comprise a primary cell culture or an immortalized cell line. The adipose tissue may be from any organism having fat tissue. In some embodiments, the adipose tissue is mammalian. In some embodiments, the adipose tissue is human. A convenient source of adipose tissue is from liposuction surgery, however, the source of adipose tissue or the method of isolation of adipose tissue is not critical to the invention.

As use herein, the terms "administration of" and or "administering" refers to the providing a compound, composition, or formulation to a subject. In some embodiments, the subject is in need of treatment. In some embodiments, it prodrug of a compound is administered.

The term "adult" as used herein, is meant to refer to any non-embryonic or non-juvenile subject. For example the term "adult adipose tissue stem cell," refers to an adipose stem cell, other than that obtained from an embryo or juvenile subject.

Cells or tissue are "affected" by an injury, disease or disorder if the cells or tissue have an altered phenotype relative to the same cells or tissue in a subject not afflicted with the injury, disease, condition, or disorder. As used herein, an "agonist" is a composition of matter that, when administered to a mammal such as a human, enhances or extends a biological activity of interest. Such effect may be direct or indirect.

A disease, condition, or disorder is "alleviated" if the severity of a symptom of the disease or disorder, the frequency with which such a symptom is experienced by a patient, or both, are reduced.

As used herein, "alleviating an injury, disease or disorder symptom," means reducing the frequency or severity of the symptom.

As used herein, an "analog" of a chemical compound is a compound that, by way of example, resembles another in structure but is not necessarily an isomer (e.g., 5-fluorouracil is an analog of thymine).

An "antagonist." is a composition of matter that when administered to a mammal such as a human, inhibits or impedes a biological activity attributable to the level or presence of an endogenous compound in the mammal. Such effect may be direct or indirect.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

"Antiviral agent," as used herein means a composition of matter which, when delivered to a cell, is capable of preventing replication of a virus n the cell, preventing infection of the cell by a virus, or reversing a physiological effect of infection of the cell by a virus. Antiviral agents are well known and described in the literature. By way of example, AZT (zidovudine. Retrovir® Glaxo Wellcome Inc., Research Triangle Park, N.C.) is an antiviral agent which is thought to prevent replication of HIV in human cells.

The term "biocompatible," as used herein, refers to a material that does not elicit a substantial detrimental response in the host.

The term "biodegradable," as used herein, means capable of being biologically decomposed. A biodegradable material differs from a non-biodegradable material in that a biodegradable material can be biologically decomposed into units which may be either removed from the biological system anchor chemically incorporated into the biological system.

The term "biological sample," as used herein, refers to samples obtained from a living organism, including skin, hair, tissue, blood, plasma, cells, sweat, and urine.

The term "biotesorbable," as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable," as the term is used herein, means that at least 80% of the total mass of material implanted is resorbed within one year. As used herein "burn" or "burns" refer to any detectable injury to tissue caused by energy applied to the tissue. The terms "burn" or "burns" further refer to any burning, or charring of the tissue, including thermal burns caused by contact with flames, hot liquids, hot surfaces, and other sources of high heat as well as steam, chemical burns, radiation, and electrical burns. First degree burns show redness; second degree burns show vesication; third degree burns show necrosis through the entire skin. Burns of the first and second degree are partial-thickness burns, those of the third degree are full-thickness burns.

The term "clearance," as used herein refers to the physiological process of removing a compound or molecule, such as by diffusion, exfoliation, removal via the bloodstream, and excretion in urine, or via sweat or other fluid.

A "compound," as used herein, refers to any type of substance or agent that is commonly considered a drug, or a candidate for use as a drug, as well as combinations and mixtures of the above.

A "control" subject is a subject having the same characteristics as a test subject, such as a similar type of dependence, etc. The control subject may, for example, be examined at precisely or nearly the same time the test subject is being treated or examined. The control subject may also, for example, be examined at a time distant from the time at which the test subject is examined, and the results of the examination of the control subject may be recorded so that the recorded results may be compared with results obtained by examination of a test subject.

A "test subject" is a subject being treated.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, bin are not limited to, radioactive isotopes, antigenic determinants, enzymes, nucleic acids available fir hybridization, chromophores, fluorophores, chemiluminescent molecules, electrochemically detectable molecules, and molecules that provide for altered fluorescence polarization or altered light scattering.

A "disease" is a state of health of an animal wherein the animal cannot maintain homeostasis, and wherein if the disease is not ameliorated then the animal's health continues to deteriorate. As used herein, normal aging is included as a disease. A "disorder" in an animal is a state of health in which the animal is able to maintain homeostasis, hut in which the animal's state of health is less favorable than it would be in the absence of the disorder. Left untreated, a disorder does not necessarily cause a further decrease in the animal's state of health.

As used herein, an "effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, a "functional" molecule is a molecule in a form in which it exhibits a property or activity by which it is characterized. A functional enzyme, for example, is one that exhibits the characteristic catalytic activity by which the enzyme is characterized.

"Graft" refers to any free (unattached) cell, tissue, or organ for transplantation. "Allograft" refers to a transplanted cell, tissue, or organ derived from a different animal of the same species.

"Xenograft" refers to a transplanted cell, tissue, or organ derived from an animal of a different species.

The term "growth factor" as used herein means a bioactive molecule that promotes the proliferation of a cell or tissue. Examples of growth factors include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8. VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue.

The term "increased oxygenation," as used herein, refers to increased oxygen levels measured at a site being treated according to the methods described herein compared with the oxygen levels at the same site prior to being treated according to the methods described herein, or as compared with the oxygen levels of a comparable site left untreated. Oxygenation of skin or the surfaces of other tissues can be measured using a saturimetry device (two very thin electrodes that are positioned on the skin) or other probe or system that measures oxygen tension or oxygen levels in tissue. Unless otherwise specified the method of determining oxygenation can be any method used to measure oxygenation. In some embodiments, the oxygenation is increased by at least 10%, 20%, 30%, 40%, or 50%. In some embodiments, the oxygenation is increased by about 5 to 20%, 10 to 20%, or 5 to 15%.

As used herein "injecting or applying" includes administration of a compound of the invention by any number of routes and means including, but not limited to, topical, oral, buccal, intravenous, intramuscular, intra arterial, intramedullar, intrathecal, intraventricular, transdermal, subcutaneous, intraperitoneal, intranasal, enteral, topical, sublingual, vaginal, ophthalmic, pulmonary, or rectal means.

As used herein, "injury" generally refers to damage, harm, or hurt; usually applied to damage inflicted on the body by an external force. As used herein, an "instructional material" includes a publication, a recording, as diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a subject. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer".

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. In some embodiments, a pharmaceutical composition comprises the compounds, compositions or formulations described herein.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The term "prevent," as used herein, means to stop something from happening, or taking advance measures against something possible or probable from happening. In the context of medicine, "prevention" generally refers to action taken to decrease the chance of getting a disease or condition.

A "prophylactic" treatment is a treatment administered, to a subject who does not exhibit signs of a disease or injury or exhibits only early signs of the disease or injury for the purpose of decreasing the risk of developing pathology associated with the disease or injury. As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "receptor" is a compound or molecule that specifically binds to a ligand.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest.

The term "skin," as used herein, refers to the commonly used definition of skin, e.g., the epidermis and dermis, and the cells, glands, mucosa, and connective tissue which comprise the skin.

By the term "specifically binds," as used herein, is meant a molecule which recognizes and binds a specific molecule, but does not substantially recognize Of bind other molecules in a sample, or it means binding between two or more molecules as in part of a cellular regulatory process, where said molecules do not substantially recognize or bind other molecules in a sample.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates When a sample is processed or subjected to purification or extraction procedures before a marker of interest is measured. Internal standards are often but are not limited to, a purified marker of interest which has been labeled, such as with a radioactive isotope, allowing it to be distinguished from an endogenous substance in a sample.

A "subject" of diagnosis or treatment is a mammal, including a human.

As used herein, a "subject in need thereof" is a patient, animal, mammal, or human, who will benefit from the method of this invention. In some embodiments, the subject in need thereof is identified as needing treatment.

A "surface active agent" or "surfactant" is a substance that has the ability to reduce the surface tension of materials and enable penetration into and through materials.

Before the present compositions and methods are described, it is to be understood that this invention is not limited to the particular processes, compositions, or methodologies described, as these may vary.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered, in some embodiments, the amount of a compound, such as the additional therapeutic, is administered in an amount that is less than the therapeutically effective amount when compared to the amount that the compound is administered as a single agent. In some embodiments, the amount is 50% of a therapeutically effective amount when administered as a single agent.

The term "thermal injury" is used interchangeably with "thermal burn" herein.

"Tissue" means (1) a group of similar cells united to perform a specific function (2) a part of an organism consisting of an aggregate of cells having a similar structure and function; or (3) a grouping of cells that are similarly characterized by their structure and function, such as muscle or nerve tissue.

The term "topical application," as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto, "Transdermal" is used interchangeably with "percutaneous."

As used herein, the term "treating" may include prophylaxis of the specific injury, disease, disorder, or condition, or alleviation of the symptoms associated with a specific injury, disease, disorder, or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein. As used herein "wound" or "wounds" may refer to any detectable break in the tissues of the body, such as injury to skin or to an injury or damage, or to a damaged site associated with a disease or disorder. Although the terms "wound" and "injury" are not always defined exactly the same way, the use of one term herein, such as "injury", is not meant to exclude the meaning of the other term.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "C1-$C_n$ alkyl" wherein a is an integer, as used herein, represents a branched or linear alkyl group having from one to the specified number of carbon atoms. Typically, C1-$C_6$ alkyl groups include, but are not limited to, methyl, ethyl, n-propyl, iso-propyl, butyl, iso-butyl sec-butyl, tert-butyl, pentyl, hexyl, and the like.

The term "C2-$C_n$ alkenyl" wherein n an integer, as used herein, represents an olefinically unsaturated branched or linear group having from two to the specified number of carbon atoms and at least one double bond. Examples of such groups include, but are not limited to, 1-propenyl, 2-propenyl, 1,3-butadienyl, 1-butenyl, hexenyl, pentenyl, and the like. The term "C2-$C_n$ alkynyl" wherein n is an integer refers to an unsaturated branched or linear group having from two to the specified number of carbon atoms and at least one triple bond. Examples of such groups include, but are not limited to, 1-propynyl, 2-propynyl, 1-butynyl, 2-butynyl, 1-pentynyl, and the like.

The term "C3-$C_n$ cycloalkyl" wherein n=8, represents cyclopropyl, cyclobutyl, cyclopentyl, cyclohexyl, cycloheptyl, and cyclooctyl.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one or more substituents. The term (C5-C8 alkyl)aryl refers to any aryl group which is attached to the parent moiety via the alkyl group.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

A "meroxapol" is polyoxypropylene-polyoxyethylene block copolymer with the general formula $HO(C_3H_6O)_a(C_2H_4O)_b(C3H_6O)_aH$. It is available in different grades. Each meroxapol name is followed by a code number according to the average numerical values of the respective monomers units denoted by "a" and "b".

As used herein, the term "optionally substituted" refers to from zero to four substituents, wherein the substituents are each independently selected. Each of the independently selected substituents may be the same or different, than other substituents.

A "poloxamer" is a nonionic polyoxyethylene-polyoxypropylene block co-polymer with the general formula $HO(C_2H4O)_a(C3H_6O)_b(C2H_4O)_aH$. It is available in different grades, which vary horn liquids to solids. Each poloxamer name is followed by a code number according to the average numerical values of the respective monomers units denoted by "a" and "b".

A "poloxamine" is a polyoxyethylen-polyoxypropylene block copolymer of ethylene diamine with the general formula $[HO(C_2H_4O)_a(C3H_6O)_bC3H_6]_2NCH_2CH_2N-[C3H_6(OC3H_6)_b(OC_2H4)_aOH]_2$. It is available in different grades. Each poloxamine name is followed by a code number according to the average numerical values of the respective monomers units denoted by "a" and "b".

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

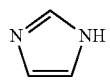

is understood to represent a mixture of the structures:

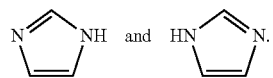

The terminology used herein is for the purpose of describing the particular versions or embodiments only, and is not intended to limit the scope of the present invention. All publications mentioned herein are incorporated by reference in their entirety.

In some embodiments, the present invention provides methods of using a surface active copolymer, including, but not limited to poloxamers, to increase oxygenation, reduce bacteria, and/or improve healing of tissues. In some embodiments, the present invention provides methods comprising the topical application of a composition or formulation comprising at least one poloxamer or other surface active copolymer to an inured or diseased site to increase oxygenation, reduce bacteria, and/or improve healing at the site. The formulation may comprise additional therapeutic agents, for example, antimicrobial agents to prevent infection, growth factors or hormones to enhance healing, drugs to treat inflammation, or anesthetics to decrease pain.

In some embodiments, the composition or formulation comprises a poloxamer (e.g. poloxamer-188 (Pluronic F68)). Not being bound by any theory, a poloxamer has the special ability to thicken at higher temperatures (such as body temperature) and liquefy at cooler temperatures (cool rinse water for example). The thickness, or viscosity, varies depending on the amount or concentration of surface active copolymer used. These properties enable it to remain resident at tissue surfaces at body temperature but also enable it to be easily removed away with cool water. In some embodiments, the surface active copolymer is biocompatible. In some embodiments, dilutions of surface active copolymers such as Poloxamer-188 (Pluronic F68) are biocompatible. In sonic embodiments, the poloxamer is present in a composition or formulation in about 0.1, 1%, 2%, 3%, 4%, 5%, 6%, 7%, 8%, 9%, 10% w/w. In some embodiments, the poloxamer is present in a composition or formulation in about 0.1-10% w/w.

Injuries, Wounds, Diseases, and Disorders

In some embodiments, the present invention provides methods of treating a site of either healthy tissue or injured tissue. The types of injuries, disease, and disorders include, but are not limited to, burns, chronic wounds, and surgical procedures such as microvascular surgery, skin flaps and skin grafts, and tissue injury resulting from, for example, a burn, scrape, cut, incision, laceration, ulcer, body piercing, bite wound, trauma, stab wound, gunshot wound, surgical wound, stretch injury, crush wound, compression wound, fracture, sprain, strain, stroke, infarction, aneurysm, herniation, isehemia, fistula, dislocation, radiation, cell, tissue or organ grafting, injuries sustained during, medical procedures, or cancer.

Such injuries include, but are not limited to, skin injury, muscle injury, brain injury, eye injury, or spinal cord injury, tissue injury can include joint injury, back injury, heart injury, vascular system injury, soft tissue injury, cartilage injury, lymphatic system injury, tendon injury, ligament injury, or abdominal injury.

The injuries that are contemplated to be treated by use of a compound, composition, or formulation as described herein, for example, any denuded area without skin or mucosa that is due to trauma such as a burn, a surgical trauma, an abrasion, a malignancy, an infection, or an allergic reaction. It is believed that the use of the composition, compound, or formulation can result in an improved cosmetic and functional outcome for the subjects being treated.

The invention encompasses treatment of all types of thermal injuries and burns. These include acute conditions such as thermal burns, chemical burns, radiation burns, burns caused by excess exposure to ultraviolet radiation such as sunburn, as well as by the chronic wounds associated with some of these conditions.

Burns include first degree burns which may cause skin manifestations such as reddening, pain, and/or mild swelling. One non-limiting example of first degree burn is a sun burn. Burns further refers to second-degree burns involving the first two layers of skin Signs of second degree burning include, among other things, deep reddening of the skin, blisters, pain, glossy appearance from leaking fluid, and possible skin loss. Burns further refers to third-degree burns which penetrate the entire thickness of the skin and may destroy tissue. Signs of third degree burning include, among other things, loss of skin, dry skin, leathery skin, charred skin having a mottled appearance, and combinations thereof. In some cases, skin with a third degree burn may be painless.

In some embodiments, compositions, compounds, or formulas disclosed herein will benefit, for example, subjects suffering from vesicant burns and, thermal burns, including first degree burns, second degree burns and third degree burns, as well as esophageal burns and erosions. For example, after cutaneous burn injury, an area surrounding the wound is the site of a pronounced inflammatory response. This "zone of stasis" undergoes progressive necrosis within 24-48 hours resulting in an expansion of the burn wound.

Injuries encompassed by the invention further include acute and chronic wounds. Chronic wounds are wounds characterized by non-healing skin wounds and include chronic venous ulcers, diabetic ulcers, arterial ulcers, pressure ulcers (e.g., decubitus ulcers) radiation ulcers, traumatic, wounds, and open, complicated non-healing wounds. Wounds further refers to cuts and scrapes known as open wounds, as well as others, such as deep bruises, or closed wounds. Non-limiting examples of wounds suitable for treatment in accordance with the present disclosure include abrasions such as those caused by; scraping the outer layer of skin; incisions such as those caused by sharp edges, knives, metal edges, broken glass or other sharp object; lacerations or jagged, irregular cuts or tears of the skin; punctures such as those caused by an object piercing the skin layers and creating a small hole; and/or burns. Additional non-limiting wounds suitable for treatment in accordance with the present disclosure include puncture wounds, gaping wounds, wounds having fatty layers, tissue or muscle, exposed, wounds having one or more foreign bodies therein, wounds causing severe pain, wounds having blood flowing therefrom, or any wound that causes numbness or loss of movement below the wound.

Other non-limiting examples of wounds suitable for treatment in accordance with the present disclosure include animal bites, arterial disease, insect stings and bites, bone infections, compromised skin/muscle gratis, gangrene, skin tears or lacerations, surgical incisions, including slow or non-healing surgical wounds, and post-operation infections. It is understood, that the listed wounds are non-limiting and that only a portion of wounds suitable for treatment in accordance with the present disclosure are listed herein. It is also contemplated that the composition of the present invention will benefit subjects with chronic skin ulcers, including but no limited to decubitus ulcers, venous stasis ulcers, arterial insufficiency ulcers, and diabetic foot ulcers.

Compositions and Formulations of the Base Surface Active Copolymer

The present invention provides for the preparation and use of pharmaceutical compositions comprising as an active ingredient a compound useful for increasing oxygenation, reducing bacteria, and/or improving healing at a tissue site. Such a pharmaceutical composition may consist of the active ingredient alone, in a form suitable for administration to a subject, or the pharmaceutical composition may comprise the active ingredient and one or more pharmaceutically acceptable carriers, one or more additional ingredients (e.g. additional therapeutic agent), or some combination of these. The active ingredient may be present in the pharmaceutical composition in the form of a physiologically acceptable ester or salt, such as in combination with a physiologically acceptable cation or anion, as is well known in the art. The present invention further contemplates the use of more than one active ingredient.

The invention is not limited to the use of poloxamer-188 (Plutonic F68) but may include the use of a different or an additional surface active copolymer, examples of which include other poloxamers, meroxapols, and poloxamines. Examples of poloxamers include, but are not limited to poloxamer-101, -105, -105 benzoate, -108, -122, -123, -124, -181, -182, -182 dibenzoate, -183, -184, -185, -188, -212, -215, -217, -231, -234, -235, -237, -238, -282, -284, -288, -331, -333, 334, -335, -338, -401, -402, -403, and -407. Examples of meroxapols include, but are not limited to, meroxapol 105, 108, 171, 172, 174, 178, 251, 252, 254, 258, 311, 312, and 314. Examples of poloxamines include, but are not limited to, poloxamine 304, 504, 701, 702, 704, 707, 901, 904, 908, 1101, 1102, 1104, 1301, 1302, 1304, 1307, 1501, 1502, 1504, and 1508.

In some embodiments, at least two different surface active copolymers are used. In one aspect, at least three different surface active copolymers are used. These combinations may include, for example, one or more poloxamers, one or more meroxapols, and one or more poloxamines. The copolymers of the invention may vary in size. The copolymer size may range, for example, from an $M_n$ of about 600 to about 20,000, or in another aspect from about 1,000 to about 10,000. In some embodiments, the weight of hydrophobic groups can be from about 45-95% by weight of the copolymer. A formulation comprising at least one copolymer a poloxamer, meroxapol, or poloxamine) and water can be prepared by cooling it to an appropriate temperature, or by other methods known in the art. Compositions of this type are described in U.S. Pat. No. 5,635,540 (Edlich et al.), hereby incorporated by reference in its entirety.

Examples of temperature ranges for preparation include, but are not limited to, from about −20° C. to about 15° C., in another aspect from about −18° C. to about 8° C., and in another aspect, from about −15° C. to about 5° C. These ranges also encompass about 0° F. to about 60° F. One of ordinary skill in the art will understand that the temperatures of preparation can be adjusted based on various criteria, such as the surface active copolymer being used, the amount or concentration being used, the type of formulation being prepared for administration, etc.

In some embodiments, the poloxamer base comprises 80% polyoxyethylene units and 20% polyoxypropylene units.

One of ordinary skill in the art will appreciate that the formulations, method of preparation, and amount of surface active copolymer used may vary, depending on the type or location of the site to be treated. For example, in some embodiments, a poloxamer, such as poloxamer-188, is mixed with water at a ratio of from 1:0.8 to 1.2 w/w. This ratio can be varied. This combination may be mixed until the powder has been wetted. The mixture may then be placed in a freezer or refrigerator and cooled, preferably for at least 4 hours. While cooling, the mixture will undergo phase transition to a liquid, as demonstrated by Edlich et al. (U.S. Pat. No. 5,635,540). The mixture is then removed from the freezer and warmed to room temperature. Pharmaceutical agents such as antimicrobials and anesthetics can be added at this point, as demonstrated by Edlich et al. (U.S. Pat. No. 5,635,540). The poloxamer base used in preparing the topical preparation can be a polyoxyalkylene based polymer based on ethylene oxide and propylene oxide and comprises a series of closely related block polymers that may generally be classified as polyoxyethylene-polyoxypropylene condensates terminated in primary hydroxyl groups. They are formed by the condensation of propylene oxide onto a propylene glycol nucleus followed by condensation of ethylene oxide onto both ends of the polyoxypropylene base. The polyoxyethylene hydrophilic groups on the ends of the molecule are controlled in length to constitute anywhere from 10% to 90% by weight of the final molecule.

In some embodiments, the molecular weight Mn of the poloxamer base ranges from about 600 to about 20,000, in some embodiments, it ranges from about 1,000 to about 10,000. In some embodiments, it ranges from about 5,000 to about 8,500.

The compositions of the present invention may comprise one or more co-additives (e.g., solvent such as water). In some embodiments, the concentration of a surface active copolymer (e.g., poloxamer 188) is about 0.01 to about 99.99% w/w. In some embodiments, it is about 1 to about 90%. In some embodiments, it is about to about 80%. In some embodiments, it is about 20% to about 70%. In some embodiments, it is about 50%. In some embodiments, it is about 5%. In some embodiments, the concentration is a % w/w as disclosed herein.

In some embodiments, a formulation or composition can be impregnated in a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient. In some embodiments, the formulation or composition can be impregnated in a wipe.

Additional Therapeutic Agents and Ingredients

The composition or formulation can further comprise additional therapeutic additives, alone or in combination (e.g., 2, 3, or 4 additional additives). Examples of additional additives include but are not limited to (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; cytokines; (g) hormones; and (h) combinations thereof.

In some embodiments, a composition or formulation comprises an antimicrobial agent. The antimicrobial agent may be provided at, for example, a standard therapeutically effective amount. A standard therapeutically effective amount is an amount that is typically used by one of ordinary skill in the art or an amount approved by a regulatory agency (e.g., the FDA or its European counterpart) Antimicrobial agents include those directed against the spectrums of gram positive organisms, gram negative organisms, fungi, and viruses. In some embodiments, the composition of formulation comprises a suitable local anesthetic agent. In some embodiments, a suitable local anesthetic agent has a melting point of 30° C. to 70° C. Examples of suitable anesthetic agents include, but are not limited prilocaine, tetracaine, butanilcaine, trimecaine, benzocaine, lidocaine, bupivocaine, dibucaine, mepivocaine, and etidocaine.

In some embodiments, the methods use at least two anesthetics. The local anesthetic composition of the present invention may further comprise suitable additives, such a pigment, a dye, an anti-oxidant, a stabilizer or a fragrance provided that addition of such an additive does not destroy the single phase of the anesthetic composition.

In some embodiments, the hydrated local anesthetic mixture is prepared by melting the local anesthetic with the higher melting point of the two, followed by addition of the other local anesthetic, under vigorous mechanical mixing, such as trituration or grinding. A milky viscous liquid is formed, at which point, the surfactant is added with more mechanical mixing. Mixing of the surfactant produces a milky liquid of somewhat lower viscosity. Finally, the balance of water is added under vigorous mechanical mixing. The material can then be transferred to an air tight container, after which a clear composition is obtained after about 60 minutes at room temperature.

Alternatively, the hydrated local anesthetic mixture can be prepared by first melting the lower melting local anesthetic, followed by addition of the other local anesthetic along with vigorous mechanical mixing, then addition of the surfactant and water as above. However, when the lower melting local anesthetic is melted first, the storage time needed to obtain the single Phase composition, increases from about 1 hour to about 72 hours.

One of ordinary skill in the art will appreciate that there are multiple suitable surfactants useful for preparing the hydrated topical anesthetic of the present invention. For example, single-phase hydrated topical anesthetics can be prepared from anionic, cationic or non-ionic surfactants.

In some embodiments, the methods comprise using a composition comprising any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, antioxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

A list of the types of drugs, and specific drugs within categories is provided below and are intended be non-limiting examples.

Antimicrobial agents include: silver sulfadiazine, Nystatin, Nystatin/triamcinolone, Bacitracin, nitrofurazone, nitrofuraritoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin (i.e., Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Eloctafenine; Flufenisal; Flunixin; Flunixin Meglamine; Flupirtine Maleate; Fluproquazone; Fluradoline Hydrochloride; Fhirbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Naturadol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olyanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salleylate; Spiradoline Mesylate; Sulentanil; Sufentanil Citrate; Talmetacin; TaInitlumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Antihypertensive: Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicoinide; Buthiazide; Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam; Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guarioxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranotol; Metolazone; Metoprolol Fumarate; Metoprolol Succinate; Metyrosine; Minoxidil; Monatepil Maleate; Muzolimine; Nebivoloi; Nitrendipine; Ofamine; Pargyline Hydrochloride; Pazoxide; Pelanserin Hydrochloride; Perindopril Ethumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinamsin Hydrochloride; Quinelorane Hydrochloride; Quinpirole Hydrochloride; Quinuelium Bromide; Ramipril; Rauwolfia Serpentina; Reseivine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Telakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine, Anti-inflammatory: Alciofenae; Alclometasone Dipropionate; Algestone Acetonide; Alpha Amylase; Amcinalal; Amcinalide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difittprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretolen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dihutyrate; Mefenamic Acid; Mesalamine; Meseclazone; Methylprednisolone Suleptanate; Momiflunate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Saicolex; Salnacedin; Salsalate; Sangauinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetretrydamine; Topinac; Tixocortol Pivalate; Tolmetin; Tolmetin Sodium; Triclonide; Triflumidate; Zidometacin; Zomepirac Sodium.

Growth Factors

In some embodiments, an effective amount if at least one growth factor, cytokine, hormone, or extracellular matrix compound or protein useful for enhancing wound healing is administered. In some embodiments, a combination of these agents is used. In some embodiments, examples of growth factors include, but are not limited to EGF, PDGF, GCSF, IL6, IL8, IL10, MCP1, MCP2, Tissue Factor, FGFb, KGF, VEGIF, PLGF, MMP1, MMP9, TIMP1, TIMP2, TGFβ, and HGF. One of ordinary skill in the art will appreciate that the choice of growth factor, cytokine, hormone, or extracellular matrix protein used will vary depending on criteria such as the type of injury, disease, or disorder being treated, the age, health, sex, and weight of the subject, etc. In some embodiments, the growth factors, cytokines, hormones, and extracellular matrix compounds and proteins are human.

Proteins and other biologically active compounds that can be incorporated into, or included as an additive within a composition or formulation described herein include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, skeletal growth factor, enzymes, or combinations and biologically active fragments thereof. Adjuvants that diminish an immune response can also be used in conjunction with the composite of the subject invention. Other molecules that can be used include, but are not limited to, growth hormones, leptin, leukemia inhibitory factor (LIF), tumor necrosis factor alpha and beta, endostatin, angiostatin, thrombospoodin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, and 18. Embodiments involving amino acids, peptides, polypeptides, and proteins may include any type of such molecules of any size and complexity as well as combinations of such molecules.

Pharmaceutical Compositions and Delivery Form

The compositions and formulations may be prepared in a variety of forms known in the art, such as liquids, aerosols, or gels. Topical administration can be performed by, for example, hand, mechanically (e.g., extrusion and spray delivery) or as a component of a dressing (e.g., gauze or other wound covering). The administration of the composition or formulation directly by hand to a tissue or biomaterial surface is preformed so as to achieve a therapeutic coating, which may be uniform, alone or in combination with an overlying dressing.

In sonic embodiments, the administration of the composition or formulation mechanically can be performed by using a device that physically pushes the composition onto a tissue or biomaterial surface so as to achieve a therapeutic coating, which may be uniform, alone or in combination with an overlying dressing.

In some embodiments, the composition or formulation can be sprayed onto a tissue or biomaterial surface so as to achieve a therapeutic coating, which may be uniform, alone or in combination with an overlying dressing. When part of a dressing, the composition or formulation is applied so as to achieve a therapeutic coating of the surface, which may be uniform.

Formulations suitable for topical administration include, but are not limited to liquid or semi-liquid preparations such as liniments, lotions oil-in-water or water-in-oil emulsions such as creams, ointments or pastes, and solutions or suspensions. Topically-administrable formulations may, for example, comprise from about 1% to about 70% (w/w) active ingredient, although the concentration of the active ingredient may be as high as the solubility limit of the active ingredient in the solvent. Formulations for topical administration may further comprise one or more of the additional ingredients described herein.

In some embodiments, a pharmaceutical cream is provided wherein a poloxamer base, in the form of powder, is mixed with water, and caused to become hydrated, by subjecting the combination of poloxamer base and water, to freezing temperatures, before an additional pharmaceutical agent such as an additional therapeutic agent is added.

In some embodiments, the present invention provides for the preparation and use of pharmaceutical compositions comprising a compound useful for treatment of various skin related injuries, trauma, diseases, disorders, or conditions described herein, including burns, wounds, surgical incisions, etc. The invention also encompasses other injuries, trauma, associated diseases and disorders other than those of the skin, including, but not limited to, gum diseases and disorders. Such a pharmaceutical composition may consist of the active ingredient alone, in a form suitable for administration to a subject, or the pharmaceutical composition may comprise at least one active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

An obstacle for topical administration of pharmaceuticals to the skin is the stratum corneum layer of the epidermis. The stratum corneum is a highly resistant layer comprised of protein, cholesterol, sphingolipids, free fatty acids and various other lipids, and includes cornified and living cells. One of the factors that limits the penetration rate (flux) of a compound through the stratum corneum is the amount of the active substance which can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The compositions or formulations described herein may be administered to, for example, a cell, a tissue, or a subject by any of several methods described herein and by others which are known to those of skill in the art.

The relative amounts of the active ingredient, the pharmaceutically acceptable carrier, and any additional ingredients in a pharmaceutical composition of the invention will vary, depending upon the identity, sex, age, size, and condition of the subject treated and further depending upon the route by which the composition is to be administered.

In addition to the active ingredient, a pharmaceutical composition of the invention may further comprise one or more additional pharmaceutically active or therapeutic agents. In some embodiments, additional agents include anti-emetics and scavengers such as cyanide and cyanate scavengers.

Controlled- or sustained-release formulations of a pharmaceutical composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Additionally, formulations for topical administration may include liquids, ointments, lotions, creams, gels (e.g., poloxamer gel), drops, suppositories, sprays, aerosols, and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Enhancers of permeation may be used. These materials increase the rate of penetration of drugs across the skin. Typical enhancers in the art include ethanol, glycerol monolaurate, PGML, (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

The source of active compound to be formulated will generally depend upon the particular form of the compound. Small organic molecules and peptidyl or oligo fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In some embodiments, the topically active pharmaceutical composition may be optionally combined with other ingredients such as moisturizers, cosmetic adjuvants, anti-oxidants, chelating agents, bleaching agents, tyrosinase inhibitors, and other known depigmentation agents, surfactants, foaming agents, conditioners, humectants, wetting agents, emulsifying agents, fragrances, viscosifiers, buffering agents, preservatives, sunscreens, and the like. In some embodiments, a permeation or penetration enhancer is included in the composition and is effective in improving the percutaneous penetration of the active ingredient into and through the stratum corneum With respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In some embodiments, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions may also contain active amounts of retinoids (i.e., compounds that bind to any members of the family of retinoid receptors), including, for example, tretinoin, retinol, esters of tretinoin and/or retinol and the like.

Although the descriptions or pharmaceutical compositions provided herein are principally directed to pharmaceutical compositions which are suitable for administration to humans, it will be understood by the skilled artisan that such compositions are generally suitable for administration, to animals of all sorts.

The present invention encompasses biologically active analogs, homologs, derivatives, and modifications of the compounds of the invention. Methods for the preparation of such compounds are known in the art.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

The composition and formulations, including but not limited to, pharmaceutical compositions, can be administered according to the methods described herein to any animal, such as a mammal (e.g. human, primates and non-primates). In seine embodiments, subjects to which administration of the pharmaceutical compositions of the invention is contemplated include, but are not limited to, humans and other primates, mammals including commercially relevant mammals such as cattle, pigs, horses, sheep, cats, and dogs.

Liquid derivatives and natural extracts made directly from biological sources may be employed in the compositions of this invention in a concentration (w/w) from about 1 to about 99%. Fractions of natural extracts and protease inhibitors may have a different preferred rage, from about 0.01% to about 20% and, more preferably, from about 1% to about 10% of the composition. Of course, mixtures of the active agents of this invention may be combined and used together in the same formulation, or in serial applications of different formulations.

The composition may comprise a preservative from about 0.005% to 2.0% by total weight of the composition. The preservative is used to prevent spoilage in the case of an aqueous gel because of repeated patient use when it is exposed to contaminants in the environment from for example, exposure to air or the patient's skin, including, contact with the fingers used for applying a composition of the invention such as a therapeutic gel or cream. Examples of preservatives useful in accordance with the invention included but are not limited to those selected from the group consisting of benzyl alcohol, sorbic acid, parabens. Unidurea, and combinations thereof. A particularly preferred preservative is a combination of about 0.5% to 2.0% benzyl alcohol and 0.05% to 0.5% sorbic acid. The composition may include an antioxidant and a chelating agent which inhibit the degradation of the compound for use in the invention in the aqueous gel formulation, Preferred antioxidants for some compounds are BHT, BHA, alphatocopherol, and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are preferred antioxidant and chelating agent respectively for some compounds, other suitable and equivalent antioxidants and chelating agents may be substituted therefor as would be known to those skilled in the art.

As used herein, "additional ingredients" include, but are not limited, to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing, or wetting agents; emulsifying agents, demulcents; buffers; salts; thickening agents; fillers; emulsifying agents; antioxidants; antibiotics antifungal agents; stabilizing agents; and pharmaceutically acceptable polymeric or hydrophobic materials. Other "additional ingredients" which may be included in the pharmaceutical compositions of the invention are known in the an and described, for example in Genaro, ed, (1985, Remington's Pharmaceutical Sciences, Mack Publishing Co., Easton, Pa.), which is incorporated herein by reference.

Other components such as preservatives, antioxidants, surfactants, absorption enhancers, viscosity enhancers or film forming polymers, bulking agents, diluents, coloring agents, flavoring agents, pH modifiers, sweeteners or taste-masking agents may also be incorporated into the composition. Suitable coloring agents include red, black, and yellow iron oxides and FD&C dyes such as FD&C Blue No. 2, FD&C Red No. 40, and the like. Suitable flavoring agents include mint, raspberry, licorice, orange, lemon, grapefruit, caramel, vanilla, cherry grape flavors, combinations thereof, and the like. Suitable pH modifiers include citric acid, tartaric acid, phosphoric acid, hydrochloric acid, maleic acid, sodium hydroxide, and the like. Suitable sweeteners include aspartame, acesulfame K, thaumatic, and the like. Suitable taste-masking agents include sodium bicarbonate, ion-exchange resins, cyclodextrin inclusion compounds, adsorbates, and the like.

Absorption enhancers for use in accordance with the present invention include, for example, polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethosdiglycol propylene glycol mono-di-caprylate, glycerol monocaprylate, glyceryl fatty acids, oleic acid, linoleic acid, glyceryl caprylate/caprate, glyceryl monooleate, glyceryl monolaurate, caprylic/capric triglycerides, ethoxylated nonylphenols. PEG-(8-50) stearates, olive oil PEG-6 esters, triolein PEG-6 esters, lecithin, d-alpha tocopheryl polyethylene glycol 1000 succinate, polycarbonate, sodium glycocholate, sodium taurocholate, cyclodextrins, citric acid, sodium citrate, triacetin, combinations thereof, and the like. In some embodiments, the absorption enhancer is triacetin. In some embodiments where an absorption enhancer is included in the formulation, the absorption enhancer is included in an amount of from about 0.001% to about 10% by weight of the formulation, preferably in an amount of about 0.01% to about 5% by weight of the formulation.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and birds including, commercially relevant birds such as chickens, ducks, geese, and turkeys.

The pharmaceutical compositions of the invention can be administered in any suitable formulation, by any suitable means, and by any suitable route of administration. Formulations suitable for topical administration include, but are not limited to, liquid or semi-liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Topical administration of compositions of the invention may include transdermal application. Transdermal application can be performed either passively or using iontophoresis or electroporation.

Compositions of the invention may be applied using transdermal patches. Transdermal patches are adhesive hacked patches laced with an effective amount of compounds of the invention. The pressure-sensitive adhesive of the matrix will normally be a solution of polyacrylate, a silicone, or polyisobutylene (PIB). Such adhesives are well known in the transdermal art. See, for instance, the Handbook of Pressure Sensitive Adhesive Technology, 2nd Edition (1989) Van Nostrand, Reinhold.

Pressure sensitive solution polyacrylate adhesives for transdermal patches are made by copolymerizing one or more acrylate monomers ("acrylate" is intended to include both acrylates and methaoylates), one or more modifying monomers, and one or more functional group-containing monomers in an organic solvent. The acrylate monomers used to make these polymers are normally alkyl acrylates of 4-17 carbon atoms, with 2-ethylhexyl acrylate, butyl acrylate, and isooctyl acrylate being preferred. Modifying monomers are typically included to alter the Tg of the polymer. Such monomers as vinyl acetate, ethyl acrylate and methacrylate, and methyl methacrylate are useful for this purpose. The functional group-containing monomer provides sites for crosslinking. The functional groups of these monomers are preferably carboxyl, hydroxy or combinations thereof. Examples of monomers that provide such groups are acrylic acid, methacrylic acid and hydroxy-containing monomers such as hydroxyethyl acrylate. The polyacrylate adhesives are preferably crosslinked using a crosslinking agent to improve their physical properties, (e.g., creep and shear resistance). The crosslinking density should be low since high degrees of crosslinking may affect the adhesive properties of the copolymer adversely. Examples of crosslinking agents are disclosed in U.S. Pat. No. 5,393,529. Solution polyacrylate pressure sensitive adhesives are commercially available under tradenames such as GELVA™ and DURO-TAK™ from 3M.

Polyisobutylene adhesives are mixtures of high molecular weight (HMW) PIB and low molecular weight (LMW) PIB. Such mixtures are described in the art, e.g., PCT/US91/02516. The molecular weight of the HMW PIB will usually be w the range of about 700,000 to 2,000,000 Da, whereas that of the LMW PIB will typically range between 35,000 to 60,000. The molecular weights referred to herein are weight average molecular weight. The weight ratio of HMW PIB to LMW PIB in the adhesive will normally range between 1:1 to 1:10. The PIB adhesive will also normally include a tackifier such as polybutene oil and high Tg, low molecular weight aliphatic resins such as the ESCOREZ™ resins available from Exxon Chemical. Polyisobutylene polymers are available commercially under the tradename VISTANEX™ from Exxon Chemical.

The silicone adhesives that may be used in forming the matrix are typically high molecular weight poly dimethyl siloxanes or polydimethyldiphenyl siloxanes. Formulations of silicone adhesives that are useful in transdermal patches are described in U.S. Pat. Nos. 5,232,702, 4,906,169, and 4,951,622.

Dosage forms for topical or transdermal administration of a compound of this invention include liquids, ointments, pastes, creams, lotions, gels, powders, solutions, sprays, aerosols, inhalants or patches. The active component is admixed under sterile conditions with a pharmaceutically acceptable carrier and any needed preservatives or buffers as may be required. Ophthalmic formulation, ear drops, eye ointments, powders, and solutions are also contemplated as being within the scope of this invention. Transdermal patches have the added advantage of providing controlled delivery of a compound to the body. Such dosage forms can be made by dissolving or dispensing the compound(s) in the proper medium. Absorption enhancers can also be used to increase the flux of the compound across the skin. The rate can be controlled by either providing a rate controlling membrane or by dispersing the compound in a polymer matrix or gel.

The ointments, pastes, creams, and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Topical administration may also be performed using iontophoresis devices. Such delivery systems eliminate needles entirely, and rely upon chemical mediators or external driving forces such as iontophoretic currents or thermal poration or sonophoresis to breach the stratum corneum the outermost layer of the skin, and deliver substances through the surface of the skin. The process of iontophoresis has found commercial use in the delivery of ionically charged therapeutic agent molecules such as pilocarpine, lidocaine, and dexamethasone. In this delivery method, ions bearing a positive charge are driven across the skin at the site of an electrolytic electrical system anode while ions bearing a negative charge are driven across the skin at the site of an electrolytic system cathode.

The present invention provides a system for the direct application of compounds of the invention, including additional therapeutic agents such as anesthetic agents, by iontophoresis for increasing oxygenation, reducing bacteria, and/or improving healing at as site while decreasing pain associated with injuries, diseases, and disorders.

In one embodiment, the methods of the invention provide a patch device with a donor or delivery chamber that is designed to be applied directly over an injury, incision, or wound site and utilizes an electric field to stimulate delivery of the active compound or additional therapeutic agents(s). The patch is sterilized so that risk of infection is minimal. Additionally, the system delivers medication in a constant manner over an extended period of time. Generally, such time periods are at least 30 minutes and may extend to as many as 96 hours. A pharmaceutical composition may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In some embodiments, such powders comprise particles wherein at least 98% of the particles by weight have a diameter greater than 0.5 nanometers and at least 95% of the particles by number have a diameter less than 7 nanometers. In some embodiments, at least 95% of the particles by weight have a diameter greater than 1 nanometer and at least 90% of the particles by number have a diameter less than 6 nanometers. Dry powder compositions, in some embodiments, include a solid fine powder diluent such as sugar and are conveniently provided in a unit dose form.

Low boiling propellants generally include liquid propellants having a boiling point of below 65° F. at atmospheric pressure. Generally, the propellant may constitute about 50% to about 99.9% (w/w) of the composition, and the active ingredient may constitute about 0.1% to about 20% (w/w) of the composition. The propellant may further comprise additional ingredients such as a liquid non-ionic or solid anionic surfactant or a solid diluent (preferably having a particle site of the same order as particles comprising the active ingredient).

Pharmaceutical compositions of the invention formulated for pulmonary delivery may also provide the active ingredient in the n of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, at flavoring agent such as saccharin sodium, a volatile oil, a buffering agent, a surface active agent, or a preservative such as methylhydroxybenzoate. The droplets provided by this route of administration can have an average an diameter in the range from about 0.1 to about 200 nanometers.

The formulations described herein as being useful for pulmonary delivery also useful for intranasal delivery of a pharmaceutical composition of the invention.

Another formulation suitable for intranasal administration is a coarse powder comprising the active ingredient and having an average particle from about 0.2 about 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as about 10% (w/w) and as much as about 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the from tablets or lozenges made using conventional methods, and may, for example, comprise about 0.1% to about 20% (w/w) active ingredient, the balance comprising an orally dissolvable or degradable composition and, optionally, one or more of the additional ingredients described herein. Alternately, formulations suitable for bucca administration may comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and may further comprise one or more of the additional ingredients described herein. Additionally, the formulation taken orally can be prepared as a pharmaceutical composition, including, but not limited to, a paste, a gel, a toothpaste, a mouthwash, a solution, an oral rinse, a suspension, an ointment, a cream, and a coating.

A pharmaceutical composition of the invention may be prepared, packaged, or sold in a formulation suitable for ophthalmic administration. Such formulations may, for example, be in the form of eye drops including, for example, a 0.1% to 10% (w/w) solution or suspension of the active ingredient an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

A pharmaceutical composition of the invention may be prepared, packaged, or sold in a formulation suitable for intramucosal administration. The present invention provides for intramucosal administration of compounds to allow passage or absorption of the compounds across mucosa. Such type of administration is useful for absorption orally (gingival, sublingual, buccal, etc.), rectally, vaginally, pulmonary, nasally, etc.

The compounds of the invention can be prepared in a formulation or pharmaceutical composition appropriate for administration that allows or enhances absorption across mucosa. Mucosal absorption enhancers include, but are not limited to, a bile salt, fatty acid, surfactant, or alcohol. In some embodiments, the permeation enhancer can be sodium cholate, sodium dodecyl sulphate, sodium deoxycholate, taurodeoxycholate, sodium glycocholate, dimethylsulfoxide, or ethanol. In some embodiments, a compound of the invention can be formulated with a mucosal penetration enhancer to facilitate delivery of the compound. The formulation can also be prepared with pH optimized for solubility, drug stability, and absorption through mucosa such as nasal mucosa, oral mucosa, vaginal mucosa, respiratory, and intestinal mucosa.

To further enhance mucosal delivery of pharmaceutical agents, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compounds include polyol compounds, such as oligo-, di- and monosaccharides such as sucrose, mannitol, lactose, L-arabinose, D-etythrose, D-ribose, D-xylose, D-mannose, D-galactose, lactulose, cellobiose, gentibiose, glycerin, and polyethylene glycol. Other examples of hydrophilic low molecular weight compounds useful as carriers within the invention include N-methylpyrrolidone, and alcohols (e.g., oligovinyl alcohol, ethanol, ethylene glycol, propylene glycol, etc.). These hydrophilic low molecular weight compounds can be used alone or in combination with one another or with other active or inactive components of the intranasal formulation.

When a controlled-release pharmaceutical preparation further contains a hydrophilic base, many options are available for inclusion. Hydrophilic polymers such as a polyethylene glycol and poly vinyl pyrrolidone, sugar alcohols such as D-sorbitol and xylitol, saccharides such as sucrose, maltose, lactulose, D-fructose, dextran, and glucose, surfactants such as polyoxyethylene-hydrogenated castor oil, polyoxyethylene polyoxypropylene glycol, and polyoxyethylene sorbitan higher fatty acid esters, salts such as sodium chloride and magnesium chloride, organic acids such as citric acid and tartaric acid, amino acids such as glycine, beta-alanine, and lysine hydrochloride, and aminosaccharides such as meglumine are given as examples of the hydrophilic base. Polyethylene glycol, sucrose, and polyvinyl pyrrolidone are preferred and polyethylene glycol are further preferred. One or a combination of two or more hydrophilic bases can be used.

The present invention contemplates pulmonary, nasal, or oral administration through an inhaler. In some embodiments, delivery from an inhaler can be a metered dose.

An inhaler is a device for patient self administration of at least one compound of the invention comprising a spray inhaler (e.g. a nasal, oral, or pulmonary spray inhaler) containing an aerosol spray formulation of at least one compound of the invention and a pharmaceutically acceptable dispersant. In some embodiments, the device is metered to disperse an amount of the aerosol formulation by forming a spray that contains a dose of at least one compound of the invention effective to treat a disease or disorder encompassed by the invention. The dispersant may be a surfactant, such as, but not limited to, polyoxyethylene fatty acid esters, polyoxyethylene fatty acid alcohols, and polyoxyethylene sorbitan fatty acid esters. Phospholipid-based surfactants also may be used.

In some embodiments the aerosol formulation is provided as a dry powder aerosol formulation in which a compound of the invention is present as a finely divided powder. The dry powder formulation can further comprise a bulking agent, such as, but not limited to, lactose, sorbitol, sucrose, and mannitol.

In some embodiments, the aerosol formulation is a liquid aerosol formulation further comprising a pharmaceutically acceptable diluent, such as, but not limited to, sterile water, saline, buffered saline and dextrose solution.

In some embodiments, the aerosol formulation further comprises at least one additional compound of the invention in a concentration such that the metered amount of the aerosol formulation dispersed by the device contains a dose of the additional compound in a metered amount that is effective to ameliorate the symptoms of disease or disorder disclosed herein when used in combination with at least a first or second compound of the invention.

Compounds of the invention can be prepared in a formulation or pharmaceutical composition appropriate for nasal administration. In some embodiments, the compounds of the invention can be formulated with a mucosal penetration enhancer to facilitate delivery of the drug. The formulation can also be prepared with pH optimized for solubility, drug stability, absorption through nasal mucosa, and other considerations.

Capsules, blisters, and cartridges for use in an inhaler or insufflator may be formulated to contain a powder mix of the pharmaceutical compositions provided herein; a suitable powder base, such as lactose or starch; and a performance modifier, such as 1-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

For administration by inhalation, the compounds for use according to the methods of the invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of e.g., gelatin for use in an inhaler or insufflator may be formulated containing a powder mix of the drugs and a suitable powder base such as lactose or starch.

The compounds may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. For example, the site to be treated can be contacted with a composition once a day, twice a day, three times a day, four times a day. The composition can be contacted with the site at least once a day for a period of 1-28 days, 1-21 days, 1-14 days, or 1-7 days. In some embodiments, the composition is contacted with the site at least once a day for at least 7, 14, 21, or 28 days.

Use of Cells

In some embodiments in which the treatment comprises cells include cells that can be cultured in vitro, derived from a natural source, genetically engineered, or produced by any other means.

In some embodiments the cells have been genetically engineered. The engineering can involve programming the cell to express one or more genes, repressing the expression of one or more genes, of both. One example of genetically engineered cells useful in the present invention is a genetically engineered cell that makes and secretes one or more desired molecules. Cells may produce substances to aid in the following non-inclusive list of purposes: inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace neurons, skin, synovial fluid, tendons, cartilage (including, but not limited to articular cartilage), ligaments, bone, muscle, organs, dura, blood vessels, bone marrow, and extracellular matrix. Various growth factors, cytokines, or other molecules may also be administered to regulate the cell and/or aid in the function of interest of that cell.

The cells of the present invention may be administered to a subject alone or in admixture with a composition useful in the repair of wounds and other defects. Such compositions include, but are not limited to bone morphogenetic proteins, hydroxyapatite/tricalcium phosphate particles (HA/TCP), gelatin, poly-L-lysine, and collagen.

In some embodiments, cells of the invention can be used in conjunction with a product such as Dermagraft.® Dermagraft® is indicated for use in the treatment of full-thickness diabetic foot ulcers greater than six weeks duration, which extend through the dermis, but without tendon, muscle, joint capsule, or bone exposure. Dermagraft® is a cryopreserved human fibroblast-derived dermal substitute; it is composed of fibroblasts, extracellular matrix, and a bioabsorbable scaffold. Dermagraft® is manufactured fron human fibroblast cells derived from newborn foreskin tissue. During the manufacturing process, the human fibroblasts are seeded onto a bioabsorbable polyglactin mesh scaffold. The fibroblasts proliferate to fill the interstices of this scaffold and secrete human dermal collagen, matrix proteins, growth factors, and cytokines to create a three-dimensional human dermal substitute containing metabolically active living cells. Dermagraft® does not contain macrophages, lymphocytes, blood vessels, or hair follicles.

In some embodiments, the invention provides a method of promoting the closure of a wound within a subject using cells and compositions as described herein. In accordance with the method, the inventive cells which have been selected or have been modified to secrete a hormone, growth factor, or other agent are transferred to the vicinity of a wound under conditions sufficient for the produce the hormone, growth factor other agent. The presence of the hormone, growth factor, or other agent in the vicinity of the wound promotes closure of the wound. In some embodiments, proliferation of the administered cells promotes healing of the wound. In some embodiments, differentiation of the administered cells promotes healing of the wound. The method promotes closure of both external surface) and internal wounds. The method need not achieve complete healing or closure of the wound; it is sufficient for the method to promote any degree of wound closure. In this respect, the method can be employed alone or as an adjunct to other methods for healing wounded tissue.

The present invention encompasses a method of treating at disorder amenable to cell therapy comprising administering to the affected subject a therapeutically effective amount of the cells of the invention.

In some embodiments, the cells obtained and cultured in order to derive and store the cells for therapeutic uses using cell therapy should the subject require, for example, disease therapy, tissue repair, transplantation, treatment of a cellular debilitation, or treatment of cellular dysfunctions in the future.

In some embodiments, cells derived from a subject are directly differentiated in vitro or in vivo to generate differentiating or differentiated cells without generating a cell line.

Such cell therapy methods encompass the use of the cells of this invention in combination with growth factors or chef chemokines such as those inducting proliferation, lineage-commitment, or genes car proteins of interest. Treatment methods may include providing stern or appropriate precursor cells directly for transplantation where the tissue is regenerated in vivo or recreating the desired tissue in vitro and then providing the tissue to the affected subject.

The composites and/or cells of the present invention can be used as a vehicle for the in situ delivery of biologically active agents. The biologically active agents incorporated into, or included as an additive within, the composite of the subject invention can include, without limitation, medicaments, growth factors, vitamins, mineral supplements, substances used for the treatment, prevention, diagnosis, cure or mitigation of disease or illness, substances which affect the structure or function of the body, or drugs. The biologically active agents can be used, for example, to facilitate implantation of the composite or cell suspension into a subject to promote subsequent integration and healing processes. The active agents include, but are not limited to, antifungal agents, antibacterial agents, anti-viral agents, anti-parasitic agents, growth factors, angiogenic factors, anesthetics, mucopolysaccharides, metals, cells, and other wound healing agents. Because the processing conditions can be relatively benign (physiological temperature and pH), live cells can be incorporated into the composite during its formation, or subsequently allowed to infiltrate the composite through tissue engineering techniques.

In some embodiments, a composition comprising the cells of the invention is administered locally by injection. Compositions comprising the cells can be further combined with known drugs, and in one embodiment, the drugs are bound to the cells. These compositions can be prepared in the form of an implantable device that can be molded to a desired shape. In one embodiment, a graft construct is prepared comprising a biocompatible matrix and one or more cells of the present invention, wherein the matrix is formed in a shape to fill a gap or space created by the removal of a tumor, injured, or diseased tissue.

The cells can be seeded onto the desired site within the tissue to establish a population. Cells can be transferred to sites in vivo using devices such as catheters, trocars, cannulae, stems (which can be seeded with the cells), etc.

The cells can be employed alone or within biologically-compatible compositions to generate differentiated tissues and structures, both in vivo and in vitro, or to stimulate a process of interest in a tissue. Additionally, the cells can be expanded and cultured to produce hormones, growth factors, including pleiotropic growth factors, cytokines, and chemokines, and to provide conditioned culture media for supporting the growth and expansion of other cell populations. In another aspect, the invention encompasses a lipo-derived lattice substantially devoid of cells, which includes extracellular matrix material form adipose tissue. The lattice can be used as a substrate to facilitate the growth and differentiation of cells, whether in vivo or in vitro, into anlagen or mature tissue or structures, as well as to provide an environment which maintains the viability of the cells.

The present invention thus provides methods and compositions for delivering incredibly huge numbers of ASCs, precursors, or differentiated cells derived from adipose tissue for the procedures and treatments described herein. Additionally, for diseases that require cell infusions or administration, adipose tissue harvest is minimally invasive, yields many cells, and can be done repeatedly The present invention encompasses the preparation and use of immortalized cell lines, including, but not limited to, adipose tissue-derived cell lines capable of differentiating into at least one cell type. Various techniques for preparing immortalized cell lines are known to those of ordinary skill in the art.

Compositions comprising cells of the invention can be employed in any suitable manner to facilitate the growth and differentiation of the desired tissue. For example, the composition can be constructed using three-dimensional or stereotactic modeling techniques. To direct the growth and differentiation of the desired structure, the composition can be cultured ex vivo in a bioreactor or incubator, as appropriate. In some embodiments, the structure is implanted within the host animal directly at the site in which it is desired, to grow the tissue or structure. In some embodiments, the composition can be engrafted onto a host, where it will grow and mature until ready for use. Thereafter, the mature structure (or anlage) is excised from the host and implanted into the host, as appropriate.

One of ordinary skill in the art would appreciate that there are other carriers useful for delivering the cells of the invention. Such carriers include, but are not limited to, calcium phosphate, hydroxyapatite, and synthetic or natural polymers such as collagen or collagen fragments in soluble or aggregated forms. In some embodiments, such carriers serve to deliver the cells to a location or to several locations. In some embodiments, the carriers and cells can be delivered either through systemic administration or by implantation. Implantation can be into one site or into several sites.

As indicated above, cells can be seeded onto and/or within the organic/inorganic composites of the present invention. Likewise, tissues such as cartilage can be associated with the composites prior to implantation within a patient. Examples of such cells include, but are not limited to, bone cells (such as osteoclasts, osteoblasts, and osteocytes), blood cells, epithelial cells, neural cells (e.g., neurons, astrocytes, and oligodendrocytes), and dental cells (odontoblasts and ameloblasts). Seeded cells can be autogenic, allogenic, or xenogeneic. Seeded cells can be encapsulated or non-encapsulated.

Additional Uses

In some embodiments, the pharmaceutical composition of the invention can be used as a cleanser. In some embodiments, the composition can be used as a wound cleanser or a skin cleanser. In some embodiments, the skin is injured or diseased. One of ordinary skill in the art will understand that the formulation used as a cleanser and its route and dosage of administration can be varied depending on the types of variables described herein.

Kits

The present invention should be construed to include kits for increasing oxygenation at a site of treatment. The invention includes a kit which in some embodiments comprises a compound identified in the invention, a standard, other materials which are used to apply the invention and/or manage the treatment site, and an instructional material which describes administering the compound and any additional components to a cell or an animal. This should be construed to include other embodiments of kits that are known to those skilled in the art, such as a kit comprising a standard and a (preferably sterile) solvent suitable for dissolving or suspending the composition of the invention prior to administering the compound to a cell or an animal. In some embodiments, the animal is a mammal, such as a human.

The compositions can also comprise other ingredients. For example, the composition can comprise components as described in U.S. Publication No. US 20090202615, which is hereby incorporated by reference in its entirety.

The present invention may be embodied in other specific forms without departing from the spirit or essential attributes thereof. This invention encompasses all combinations of the different aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

The examples provided throughout his application are non-inclusive unless otherwise stated. They include but are not limited to the recited examples.

The previous description of the disclosed embodiments is provided to enable any person skilled in the art to make or use the present invention. Various modifications to these embodiments will be readily apparent to those skilled in the art, and the generic principles defined, herein may be applied to other embodiments without departing from the spirit or scope of the invention. Accordingly, the present invention is not intended to be limited to the embodiments shown herein but is to be accorded the widest scope consistent with the principles and novel features disclosed herein.

Embodiments of the invention may also include formulations of poloxamer with additional components, examples of which are disclosed in the following tables. The invention is not limited to these examples. For example, in some embodiments, the composition or formulation comprises the formulation as disclosed in Formulations A, B, C, D, E, F, G, H, I, J, K, L, M, N, O, P, Q, S, T, U. These formulations can be prepared as liquids, gels or be impregnated into various fabrics, including, but not limited to, dressings, wipes, and the like. The formulations can be also be directly applied (topically) to the site as a liquid or a gel. The ingredients listed in the formulations described herein can be combined sequentially or simultaneously.

| Ingredients (range) | Formulation: | | | | | | |
|---|---|---|---|---|---|---|---|
| | A | B | C | D | E | F | G |
| Water alone or with additional ingredients (balance) | — | — | — | — | — | — | — |
| *Aloe Barbadensis* Leaf Extract (0-30%) | 17% | 15.33% | 13.67% | 12% | 10.33% | 8.67% | 7% |
| Linoleamidopropyl Pg-Dimonium Chloride Phosphate (0-20%) | 1.33% | 1.33% | 1.33% | 1.33% | 1.33% | 1.33% | 1.33% |
| Polysorbate 20 (0-10%) | 0.44% | 0.44% | 0.44% | 0.44% | 0.44% | 0.44% | 0.44% |
| Sodium Coco-Pg Dimonium Chloride Phosphate (0-30%) | 0.44% | 0.44% | 0.44% | 0.44% | 0.44% | 0.44% | 0.44% |
| Allantoin (0-20%) | 0.36% | 0.36% | 0.36% | 0.36% | 0.36% | 0.36% | 0.36% |
| Disodium EDTA (0-5%) | 0.18% | 0.18% | 0.18% | 0.18% | 0.18% | 0.18% | 0.18% |
| Sodium Benzoate (0-5%) | 0.13% | 0.13% | 0.13% | 0.13% | 0.13% | 0.13% | 0.13% |
| Benzalkonium Chloride (0-5%) | 0.10% | 0.10% | 0.10% | 0.10% | 0.10% | 0.10% | 0.10% |
| Fragrance (0-5%) | 0.06% | 0.06% | 0.06% | 0.06% | 0.06% | 0.06% | 0.06% |
| Iodopropynyl Butylcarbamate (0-5%) | 0.17% | 0.17% | 0.17% | 0.17% | 0.17% | 0.17% | 0.17% |
| Poloxamer 188 (0.01-75%) | 75.0% | 70% | 65% | 60% | 55% | 50% | 45% |

| Ingredients | Formulation: | | | | | | |
|---|---|---|---|---|---|---|---|
| | H | I | J | K | L | M | N |
| Water alone or with additional ingredients (balance) | — | — | — | — | — | — | — |
| *Aloe Barbadensis* Leaf Extract (0-30%) | 5.33% | 5.33% | 2% | 2% | 3.67% | 5.33% | 7.00% |
| Linoleamidopropyl Pg-Dimonium Chloride Phosphate (0-20%) | 1.33% | 1.33% | 1.33% | 1.33% | — | 12.33% | 15% |
| Polysorbate 20 (0-10%) | 0.44% | 0.44% | 0.44% | 0.44% | 0.44% | 0.44% | 0.44% |
| Sodium Coco-Pg Dimonium Chloride Phosphate (0-30%) | 0.44% | 0.44% | 0.44% | 0.44% | 0.44% | 0.44% | 0.44% |
| Allantoin (0-20%) | 0.36% | 0.36% | 0.36% | 2% | 2% | 2% | 2% |

-continued

| | | | | | | | |
|---|---|---|---|---|---|---|---|
| Disodium EDTA (0-5%) | 0.18% | 0.18% | 0.18% | 0.18% | 0.18% | 0.18% | 0.18% |
| Sodium Benzoate (0-5%) | 0.13% | 0.13% | 0.13% | 0.13% | 0.13% | 0.13% | 0.13% |
| Benzalkonium Chloride (0-5%) | 0.1% | 0.2% | 0.3% | 0.4% | 0.5% | 1% | 2% |
| Fragrance (0-5%) | 0.06% | 0.06% | 0.06% | — | — | — | — |
| Iodopropynyl Butylcarbamate (0-5%) | 0.17% | 0.17% | 0.17% | 0.15% | 0.15% | 0.15% | 0.15% |
| Poloxamer 188 (0.01-75%) | 5% | 5% | 0.1% | 40.0% | 35% | 30% | 25% |

| | Formulation: | | | | | | |
|---|---|---|---|---|---|---|---|
| Ingredients | O | P | Q | R | S | T | U |
| Water alone or with additional ingredients (balance) | — | — | — | — | — | — | — |
| *Aloe Barbadensis* Leaf Extract (0-30%) | 8.67% | 10.33% | 12% | 30% | 15.33% | 17% | 20% |
| Linoleamidopropyl Pg-Dimonium Chloride Phosphate (0-20%) | 1% | 5% | 7.5% | 20% | 15% | 17.5% | 10% |
| Polysorbate 20 (0-10%) | 0.1% | 1% | 4% | 6% | 8% | 9% | 10% |
| Sodium Coco-Pg Dimonium Chloride Phosphate (0-30%) | 1% | 5% | 7.5% | 10% | 15% | 17.5% | 20% |
| Allantoin (0-20%) | 2% | 4% | 8% | 20% | 15% | 18% | 12% |
| Disodium EDTA (0-5%) | 0.15% | 0.8% | 1.5% | 2% | 3% | 4.5% | 5% |
| Sodium Benzoate (0-5%) | 0.1% | 0.15% | 2% | 3.13% | 3.38% | 4% | 5% |
| Benzalkonium Chloride (0-5%) | 0.15% | 0.5% | 0.75% | 1.5% | 1.5% | 1.75% | 2% |
| Fragrance (0-5%) | — | — | — | — | — | — | — |
| Iodopropynyl Butylcarbamate (0-5%) | 0.15% | 0.5% | 0.75% | 1.5% | 1.5% | 0.75% | 2% |
| Poloxamer 188 (0.01-75%) | 20% | 15% | 10% | 5% | 2.5% | 1% | 1% |

EXAMPLE

Example 1

A patient with a wound is cleansed with a wipe comprising a composition comprising a formulation selected from Formulations A-U. The wipe is impregnated with the formulation. The treatment lasts two weeks. Bacterial population are evaluated by taking samples by plug, the wound area reduction is visualized using the Visitrak™ system and the variation in oxygen saturimetry is determined using a reflectance saturimeter. The results demonstrate significant clinical improvement, particularly in terms of oxygen saturimetry improvement. Oxygen saturation increases by at least 5-10%. Bacterial count is also reduced. Cleansing and hydration of the perilesional area and border of the wound with the wipe contributes to the healing process. This is determined by evaluating, the level of oxygen in the perilesional tissue areas. An increase of the level of oxygen in the perilesional area is recorded. The efficacy in the reduction of the bacterial count is satisfactory. In colonized wounds, significant clinical improvement are recorded, comparable in percentage terms to the improvements that are recorded on clean wounds. The activity of the formulation is evident from the clinical evaluation and from the oxygen levels that are recorded in the perilesional areas. Without wishing to be bound by theory, it is hypothesized that the surfactant component acts as an oxygen reservoir and/or delivery vehicle to increase oxygenation, reduce bacteria, and improve healing.

What is claimed is:

1. A method for increasing oxygenation of a wound, comprising topically administering a composition selected from the group consisting of formulations A-U, wherein formulation A is: 17% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.10% benzalkonium chloride, 0.06% fragrance, 0.17% iodopropynyl butylcarbamate, and 75.0% poloxamer 188;

formulation B is: 15.33% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18%, disodium EDTA, 0.13% sodium benzoate, 0.10% benzalkonium chloride, 0.06% fragrance, 0.17% iodopropynyl butylcarbamate, and 70.0% poloxamer 188;

formulation C is: 13.67% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.10% benzalkonium chloride, 0.06% fragrance, 0.17% iodopropynyl butylcarbamate, and 65.0% poloxamer 188;

formulation D is: 12% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.10% benzalkonium chloride, 0.06% fragrance, 0.17% iodopropynyl butylcarbamate, and 60.0% poloxamer 188;

formulation E is: 10.33% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.10% benzalkonium chloride, 0.06% fragrance, 0.17% iodopropynyl butylcarbamate, and 55.0% poloxamer 188;

formulation F is: 8.67% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.10% benzalkonium chloride, 0.06% fragrance, 0.17% iodopropynyl butylcarbamate, and 50.0% poloxamer 188;

formulation G is: 7% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.10% benzalkonium chloride, 0.06% fragrance, 0.17% iodopropynyl butylcarbamate, and 45.0% poloxamer 188;

formulation H is: 5.33% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.10% benzalkonium chloride, 0.06% fragrance, 0.17% iodopropynyl butylcarbamate, and 5.0% poloxamer 188;

formulation I is: 5.33% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.20% benzalkonium chloride, 0.06% fragrance, 0.17% iodopropynyl butylcarbamate, and 5.0% poloxamer 188;

formulation J is: 2.0% aloe barbadensis leaf extract, 1.33% linoleamidopropyl pg-dimonium chloride phosphate, 0.44% polysorbate 20, 0.44% sodium coco-pg dimonium chloride phosphate, 0.36% allantoin, 0.18% disodium EDTA, 0.13% sodium benzoate, 0.30% benzalkonium chloride, 0.06% fragrance, 0.17% iodopropynyl butylcarbamate, and 0.1% poloxamer 188;

formulation K is: 2% aloe barbadensis leaf extract, 1.33% linoleamidopropyl pg-dimonium chloride phosphate, 0.44% polysorbate 20, 0.44% sodium coco-pg dimonium chloride phosphate, 2% allantoin, 0.18% disodium EDTA, 0.13% sodium benzoate, 0.40% benzalkonium chloride, 0.15% iodopropynyl butylcarbamate, and 40.0% poloxamer 188;

formulation L is: 3.67% aloe barbadensisl extract, 0.44% polysorbate 20, 0.44% sodium coco-pg dimonium chloride phosphate, 2.0% allantoin, 0.18% disodium EDTA, 0.13% sodium benzoate, 0.50% benzalkonium chloride, 0.15% iodopropynyl butylcarbamate, and 35.0% poloxamer 188;

formulation M is: 5.33% aloe barbadensis leaf extract, 12.33% linoleamidopropyl pg-dimonium chloride phosphate, 0.44% polysorbate 20, 0.44% sodium coco-pg dimonium chloride phosphate, 2.0% allantoin, 0.18% disodium EDTA, 0.13% sodium benzoate, 1.0% benzalkonium chloride, 0.15% iodopropynyl butylcarbamate, and 30.0% poloxamer 188;

formulation N is: 7.0% aloe barbadensis leaf extract, 15% linoleamidopropyl pg-dimonium chloride phosphate, 0.44% polysorbate 20, 0.44% sodium coco-pg dimonium chloride phosphate, 2.0% allantoin, 0.18% disodium EDTA, 0.13% sodium benzoate, 2.0% benzalkonium chloride, 0.15% iodopropynyl butylcarbamate, and 25.0% poloxamer 188;

formulation O is: 8.67% aloe barbadensis leaf extract, 1.0% linoleamidopropyl pg-dimonium chloride phosphate, 0.10% polysorbate 20, 1.0% sodium coco-pg dimonium chloride phosphate, 2.0% allantoin, 0.15% disodium EDTA, 0.10% sodium benzoate, 0.15% benzalkonium chloride, 0.15% iodopropynyl butylcarbamate, and 20% poloxamer 188;

formulation P is: 10.33% aloe barbadensis leaf extract, 5% linoleamidopropyl pg-dimonium chloride phosphate, 1.0% polysorbate 20, 5.0% sodium coco-pg dimonium chloride phosphate, 4.0% allantoin, 0.80% disodium EDTA, 0.15% sodium benzoate, 0.50% benzalkonium chloride, 0.5% iodopropynyl butylcarbamate, and 15.0% poloxamer 188;

formulation Q is: 12% aloe barbadensis leaf extract, 7.5% linoleamidopropyl pg-dimonium chloride phosphate, 4.0% polysorbate 20, 7.5% sodium coco-pg dimonium chloride phosphate, 8.0% allantoin, 1.5% disodium EDTA, 2.0% sodium benzoate, 0.75% benzalkonium chloride, 0.75% iodopropynyl butylcarbamate, and 10.0% poloxamer 188;

formulation R is: 30% aloe barbadensis leaf extract, 20% linoleamidopropyl pg-dimonium chloride phosphate, 6.0% polysorbate 20, 10% sodium coco-pg dimonium chloride phosphate, 20% allantoin, 2.0% disodium EDTA, 3.13% sodium benzoate, 1.5% benzalkonium chloride, 1.5% iodopropynyl butylcarbamate, and 5.0% poloxamer 188;

formulation S is: 15.33% aloe barbadensis leaf extract, 15% linoleamidopropyl pg-dimonium chloride phosphate, 8.0% polysorbate 20, 15% sodium coco-pg dimonium chloride phosphate, 15% allantoin, 3.0% disodium EDTA, 3.38% sodium benzoate, 1.5% benzalkonium chloride, 1.5% Iodopropynyl butylcarbamate, and 2.5% poloxamer 188:

formulation T is: 17% aloe barbadensis leaf extract, 17.5% linoleamidopropyl pg-dimonium chloride phosphate, 9% polysorbate 20, 17.5% sodium coco-pg dimonium chloride phosphate, 18% allantoin, 4.5% disodium EDTA, 4% sodium benzoate, 1.75% benzalkonium chloride, 1.75% iodopropynyl butylcarbamate, and 1.0% poloxamer 188;

formulation U is: 20% aloe barbadensis leaf extract, 10% linoleamidopropyl pg-dimonium chloride phosphate, 10% polysorbate 20, 20% sodium coco-pg dimonium chloride phosphate, 12% allantoin, 5.0% disodium EDTA, 5.0% sodium benzoate, 2.0% benzalkonium chloride, 2.0% iodopropynyl butylcarbamate, and 1.0% poloxamer 188, and wherein the composition further comprises about 10% to about 50% of a standard therapeutically effective amount of at least one therapeutic agent selected from the group consisting of antimicrobial agent, analgesics, and combinations thereof to the wound.

* * * * *